(12) United States Patent
    Haines

(10) Patent No.: US 12,672,937 B2
(45) Date of Patent: *Jul. 7, 2026

(54) CONFIGURABLE COUNTERBALANCE MECHANISM

(71) Applicant: Intuitive Surgical Operations, Inc., Sunnyvale, CA (US)

(72) Inventor: Timothy P. Haines, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/083,258

(22) Filed: Mar. 18, 2025

(65) Prior Publication Data

US 2025/0302578 A1    Oct. 2, 2025

Related U.S. Application Data

(63) Continuation of application No. 17/829,261, filed on May 31, 2022, now Pat. No. 12,279,920.
    (Continued)

(51) Int. Cl.
    *A61B 90/50*      (2016.01)
    *A61B 34/00*      (2016.01)
    *A61B 34/35*      (2016.01)

(52) U.S. Cl.
    CPC .............. *A61B 90/50* (2016.02); *A61B 34/35* (2016.02); *A61B 2034/715* (2016.02);
    (Continued)

(58) Field of Classification Search
    CPC ............ A61B 90/50; A61B 2090/5025; A61B 2090/504; A61B 2034/715; A61B 34/35;
    (Continued)

(56) References Cited

U.S. PATENT DOCUMENTS 2,910,335 A    10/1959  Wales
3,266,216 A    8/1966  Den et al.
    (Continued)

OTHER PUBLICATIONS

Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Jonathan Liu
*Assistant Examiner* — Guang H Guan
(74) *Attorney, Agent, or Firm* — IP Spring

(57)    ABSTRACT

Implementations relate to a configurable counterbalance mechanism. In some implementations, a counterbalance apparatus includes a spring, a tension element coupled between the spring and a mechanical ground, a base element coupled to a load, and a configurable arm rotatably coupled to the base element. A first pulley and a second pulley are rotatably coupled to the configurable arm, the second pulley orbitable about the first axis, and the tension element is at least partially wrapped around the first pulley and the second pulley. The configurable arm is rotatably configurable at either a first orientation or a second orientation, where the first orientation is associated with a center of gravity of the load located on a first side of the counterbalance apparatus and the second orientation is associated with the center of gravity of the load located on a second side of the counterbalance apparatus opposite to the first side.

20 Claims, 17 Drawing Sheets

Related U.S. Application Data

(60) Provisional application No. 63/195,407, filed on Jun. 1, 2021.

(52) U.S. Cl.
CPC ................ *A61B 2090/5025* (2016.02); *F16M 2200/041* (2013.01); *F16M 2200/066* (2013.01)

(58) Field of Classification Search
CPC .... F16M 11/06; F16M 11/18; F16M 2200/04; F16M 2200/041; F16M 2200/042; F16M 2200/044; F16M 2200/045; F16M 2200/047; F16M 2200/048; F16M 2200/066; F16M 2200/068
See application file for complete search history.

(56) References Cited

U.S. PATENT DOCUMENTS

| | | | |
|---|---|---|---|
| 4,483,126 A | | 11/1984 | Henry |
| 5,538,214 A | | 7/1996 | Sinila |
| 6,714,839 B2 | | 3/2004 | Salisbury, Jr. et al. |
| 7,428,855 B2 | | 9/2008 | Duval |
| 7,837,674 B2 | | 11/2010 | Cooper |
| 8,220,765 B2 | | 7/2012 | Bailey |
| 8,490,953 B2 | | 7/2013 | Luke et al. |
| 9,050,119 B2 | | 6/2015 | Devengenzo et al. |
| 9,301,807 B2 | | 4/2016 | Duval |
| 9,510,798 B2 | | 12/2016 | Mao et al. |
| 9,850,994 B2 | | 12/2017 | Schena |
| 9,877,792 B2 | | 1/2018 | Cooper |
| 9,949,604 B2 | | 4/2018 | Quinn et al. |
| 10,682,193 B2 | | 6/2020 | Choi et al. |
| 11,788,675 B2 | | 10/2023 | Hung |
| 11,919,153 B2 | | 3/2024 | Liao et al. |
| 11,937,890 B2 | | 3/2024 | Martin |
| 12,023,205 B2 | | 7/2024 | Martin et al. |
| 12,279,920 B2 * | | 4/2025 | Haines ............... F16M 11/2064 |
| 2022/0378546 A1 | | 12/2022 | Haines |
| 2024/0157585 A1 | | 5/2024 | Liao et al. |
| 2025/0302578 A1 * | | 10/2025 | Haines ................... A61B 34/71 |

\* cited by examiner

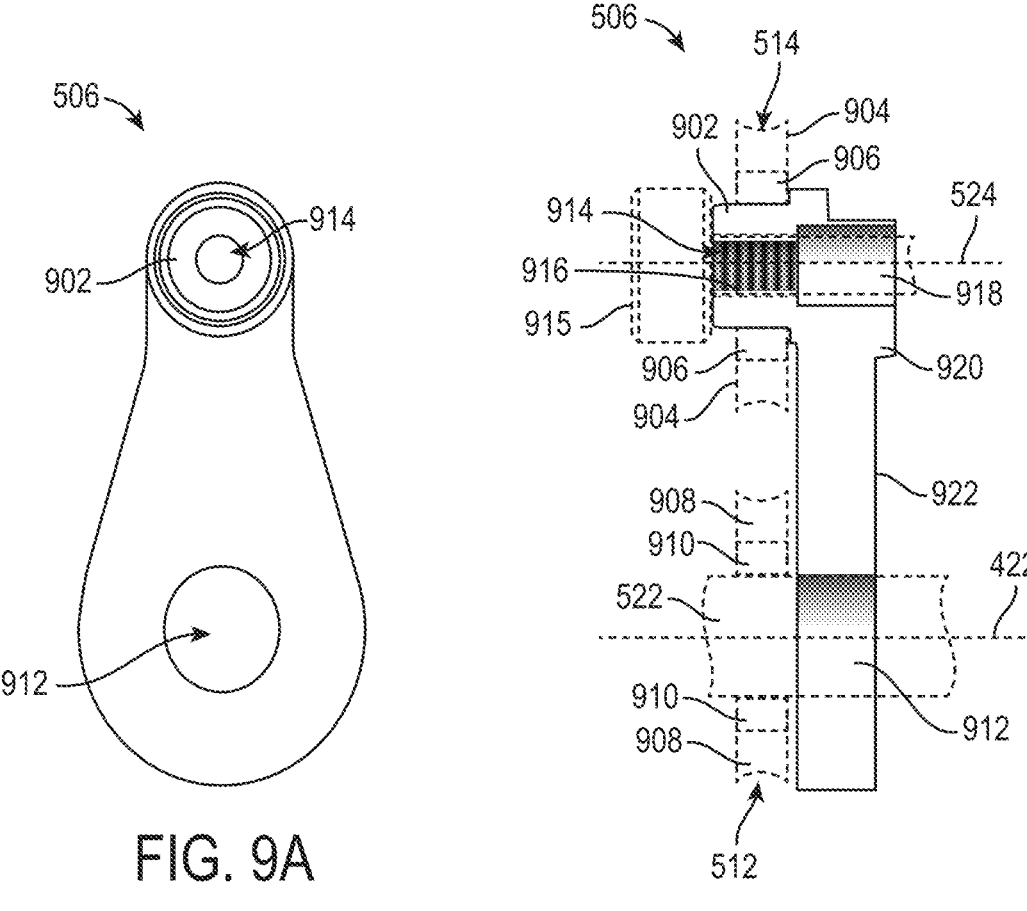
FIG. 9A
FIG. 9B
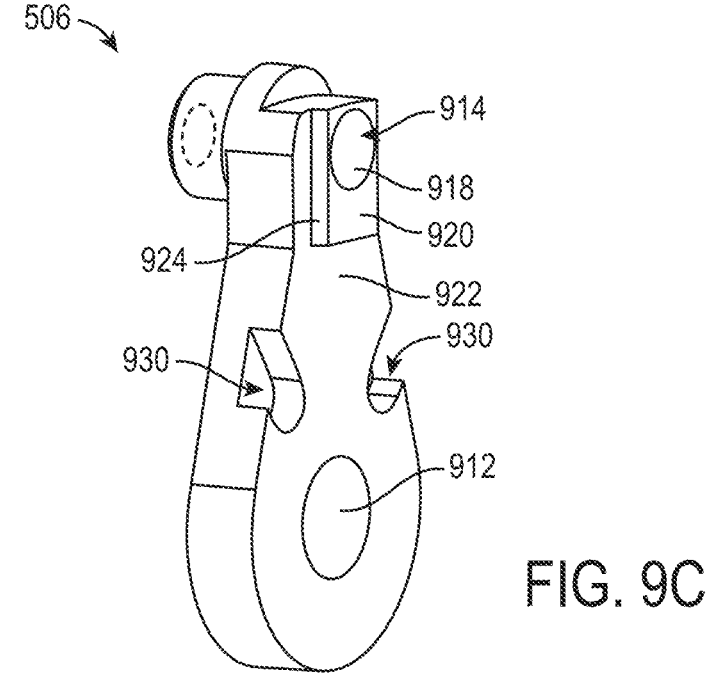
FIG. 9C

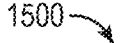

1500

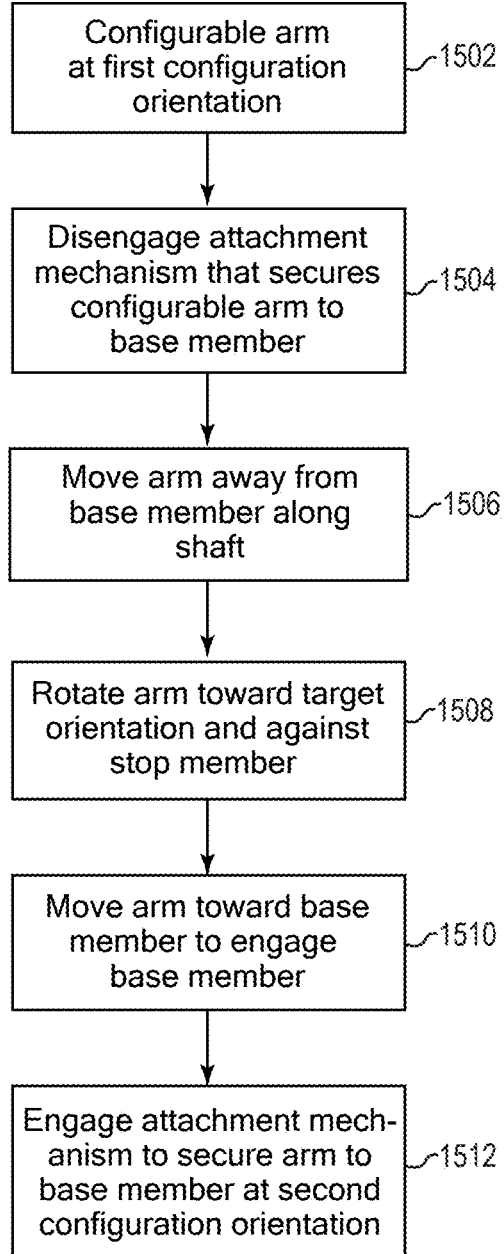

| Configurable arm at first configuration orientation | 1502 |

↓

| Disengage attachment mechanism that secures configurable arm to base member | 1504 |

↓

| Move arm away from base member along shaft | 1506 |

↓

| Rotate arm toward target orientation and against stop member | 1508 |

↓

| Move arm toward base member to engage base member | 1510 |

↓

| Engage attachment mechanism to secure arm to base member at second configuration orientation | 1512 |

FIG. 15

CONFIGURABLE COUNTERBALANCE MECHANISM

CROSS-REFERENCE TO RELATED APPLICATIONS

The present application is a continuation of U.S. patent application Ser. No. 17/829,261, filed May 31, 2022 and titled "Configurable Counterbalance Mechanism," which claims priority to U.S. Provisional Patent Application No. 63/195,407, filed Jun. 1, 2021 and titled "Configurable Counterbalance Mechanism," the entire contents of both of which are hereby incorporated by reference.

BACKGROUND

Load positioning systems can be used in a variety of applications. In one example, a control input device can include a grip held by a user, where the grip is connected to a mechanical linkage such as a mechanical arm. The grip can be moved by the user in one or more degrees of freedom provided by the mechanical arm to provide input to a system, such that the user contact on the grip acts as a load on the mechanical arm. In some examples, the grip is included in a control input device that can be manipulated by a user to control functions of a manipulator device, including movement and other operations of the manipulator device. For example, forces can be applied to the mechanical arm by motors to provide force feedback to the control input device and/or to position the grip in a particular workspace. For example, input control devices can be used in teleoperated systems such as teleoperated surgical devices that allow the user to control various types of medical instruments at a surgical site to perform surgical procedures. Other teleoperated systems can also make use of control input devices to allow a user to control one or more manipulator devices at a worksite. In other examples, load positioning systems can be provided at the manipulator device of a teleoperated system, e.g., at mechanical linkages of the manipulator device used to move and hold various end effectors such as surgical instruments or other tools. Further, load positioning systems can be used in other types of control input devices and other devices that are not part of a teleoperated system.

In some implementations of load positioning systems, a counterbalance force is applied to the mechanical arm by a counterbalance mechanism to compensate for the effects of gravity on the mechanical arm. For example, the counterbalance mechanism can include springs that provide the counterbalance force. In some examples, the use of a counterbalance mechanism allows gravity compensation when motors are not powered, and allows forces of lower magnitude to be output by the motors to the mechanical arm since the motors need not provide as much counterbalance forces themselves to compensate for gravity. In one example, the counterbalance mechanism may provide a reduction in the speed and/or magnitude of motion of the arm falling through space, e.g., when the user removes his or her grip from an input control device connected to the arm.

In some systems, a user control system can include a left input control device and a right input control device that are positioned to be manipulated by a user's left hand and right hand, respectively. The left input control device may have a different configuration than the right input control device to accommodate the associated hand. For example, the counterbalance mechanism of a control device has a configuration based on a center of gravity of the control input device that the mechanism is balancing. This configuration is changed based on whether the control input device is for left-handed use or right-handed use. For example, the center of gravity of the counterbalanced load can be on opposite sides of the counterbalance mechanism for the left-handed and right-handed configurations.

One previous method to reconfigure the counterbalance mechanism for left or right handed use of a control input device includes moving a lower pulley (including a rotating pulley and a grounded cylinder) of the counterbalance mechanism with reference to the other pulleys of the counterbalance mechanism, thus providing left handed and right handed configurations for the device. For example, in the da Vinci Xi® surgical system's surgeon console, commercialized by Intuitive Surgical, Inc., the lower pulley is moved to either side of a vertical equilibrium axis of the load depending on the selected configuration. However, this counterbalance mechanism is limited in its reconfiguring ability to the available space in which the lower pulley may be moved. For example, this mechanism may not be suitable for implementations in which the counterbalanced load has a center of gravity that is located a large distance away from the vertical axis that intersects the axis of rotation of the load (the vertical equilibrium position of the load). In some examples, such a center of gravity location can be caused by a load having a heavy mass, or having extended portions or uncompacted form. When using the previous counterbalance mechanism for such a load, moving the lower pulley by a larger amount would be required in response to the center of gravity being changed. However, such larger lower pulley movement may not be possible due to constraints of a housing or packaging of the mechanical arm. Such counterbalance mechanisms do not enable fast and easy changes to its components to accommodate such a change of location of a load that has a center of gravity farther from the vertical axis of the counterbalance mechanism.

Furthermore, the cable of this previous counterbalance mechanism remains in place when the lower pulley is moved in position. Thus, the tension in the cable, as indicated by the stretch of the counterbalance spring when the load is in a home position, is higher in one configuration than in the other configuration. This counterbalance mechanism therefore provides different gravity counterbalance performance in one configuration than in the other, causing inconsistency in performance. In some cases, counterbalance mechanisms may be specifically produced for left-handed or right-handed use, causing inefficiency in production and maintenance of control input devices.

In addition, existing counterbalance mechanisms may produce counterbalance forces that inaccurately counter gravity forces on a load at all rotational angles of the load and also may introduce undesired friction in the motion of the counterbalanced load. For example, a cable that wraps around the pulleys of a counterbalance mechanism may wrap around one pulley or element at one level or height, and wrap around a different pulley or element at a different level or height. This can cause inaccuracies in the produced counterbalance force since the counterbalance mechanism is typically designed without taking account of such a difference in levels. In addition, the difference in levels can cause the cable to skew out of the center of the groove located in its outer circumference and rub against sides of the groove, causing friction in the movement of the cable and in the rotation of the load about an axis.

SUMMARY

Implementations of the present application relate to a configurable counterbalance mechanism. In some implementations, a counterbalance apparatus includes a spring and a tension element including a first end coupled to the spring and a second end coupled to a mechanical ground. The apparatus includes a base element coupled to a load and a configurable arm that includes a first portion and a second portion, the first portion being rotatably coupled to the base element, and the configurable arm being rotatable about a first axis. A first pulley is rotatably coupled to the first portion and rotatable about the first axis, and a second pulley is rotatably coupled to the second portion and is rotatable about a second axis and orbitable about the first axis. The tension element is at least partially wrapped around the first pulley and the second pulley, and the configurable arm is rotatably configurable about the first axis at one of a first orientation and a second orientation. The first orientation is associated with a center of gravity of the load located on a first side of the counterbalance apparatus, and the second orientation is associated with the center of gravity located on a second side of the counterbalance apparatus that is opposite to the first side.

Various implementations and examples of the counterbalance apparatus are described. For example, in some implementations, a third axis intersects the first axis, the second axis, and a center of gravity of the load. In some implementations, the configurable arm includes a length defined by the first portion and the second portion, and the length aligned with a third axis that intersects the first axis, the second axis, and the center of gravity of the load. In some implementations, the counterbalance apparatus further includes a first stop member associated with the first orientation of the configurable arm and a second stop member associated with the second orientation of the configurable arm, the first stop member being located in a path of clockwise rotation of the configurable arm about the first axis, and the second stop member being located in a path of counterclockwise rotation of the configurable arm about the first axis. In some implementations, the first portion of the configurable arm is rotatably coupled to the base element by a shaft. In some implementations, the base element is a joint gear that is rigidly coupled to a rotatable shaft having a length and an axis of rotation, the configurable arm is rotatably coupled to the rotatable shaft, and the second pulley is coupled to the second portion of the configurable arm such that the second axis of the second pulley is at a location offset from the axis of rotation of the rotatable shaft.

In some implementations, the base element includes a first slot and a second slot, and the configurable arm engages with the first slot at the first orientation and engages with the second slot at the second orientation of the configurable arm. In some implementations, the configurable arm includes a plug portion that includes first tapered sides engageable with second tapered sides of the first slot and the second slot of the base element. In some implementations, the second portion of the configurable arm includes a first aperture, the first aperture includes a threaded portion and a clearance portion, and a bolt extends through the first pulley, through the first aperture, and into a second aperture of the base element. In some implementations, the first orientation of the configurable arm counterbalances the center of gravity of the load located on the first side of the counterbalance apparatus, and the second orientation of the configurable arm counterbalances the center of gravity of the load located on the second side of the counterbalance apparatus. In some implementations, the tension element is a cable.

In some implementations, the counterbalance apparatus further includes a third pulley rotatably coupled to the mechanical ground, and the tension element is wrapped at least partially around the third pulley prior to being wrapped around the second pulley in a path of the first end to the second end of the tension element. In some implementations, the counterbalance apparatus further includes a fourth pulley rotatably coupled to the mechanical ground, and the tension element is wrapped at least partially around the fourth pulley prior to being wrapped around the third pulley in the path of the first end to the second end of the tension element.

In some implementations, the counterbalance apparatus further includes a curved element coupled to the mechanical ground and having a curved surface, and a third pulley rotatably coupled to the curved element and rotatable about a third axis of rotation that is nonparallel to the first axis and the second axis; wherein, in a path from a first end to a second end of the tension element, the tension element is wrapped at least partially around the third pulley prior to being wrapped around the second pulley, and the tension element is at least partially wrapped around the curved element prior to being coupled to the mechanical ground at the second end of the tension element; and along the path from the first end to the second end of the tension element, the tension element exits contact with the third pulley and enters contact with the curved surface of the curved element at points located within a plane that includes the first pulley and the second pulley. In some examples, the plane is orthogonal to the first axis and the second axis, and the third axis of rotation is at a non-orthogonal angle with reference to the plane. In some examples, the curved element is rigidly coupled to the mechanical ground, is centered on the third axis, and is located between the third pulley and the mechanical ground, the curved surface of the curved element having a radius equal to a radius of the third pulley. In some implementations, the counterbalance apparatus further includes a fourth pulley rotatably coupled to the mechanical ground and rotatable about a fourth axis, the tension element is wrapped at least partially around the fourth pulley prior to being wrapped around the third pulley in the path from the first end to the second end of the tension element, and the fourth axis is nonparallel to the first axis, the second axis, and the third axis.

In some implementations, the first portion of the configurable arm includes an edge and a slot in the edge, the slot configured to receive a separation tool to slide or pry the configurable arm away from the base element. In some implementations, the load includes a mechanical member rigidly coupled to the base element, the mechanical member being rotatable about the first axis. In some implementations, the counterbalance apparatus is included in a component of a teleoperated surgical system.

In some implementations a method to configure a counterbalance mechanism includes disengaging an attachment mechanism that secures a configurable arm of the counterbalance mechanism to a base element of the counterbalance mechanism at a first orientation of the configurable arm about an axis, the base element being rigidly coupled to a load of the counterbalance mechanism. The counterbalance mechanism includes a first pulley rotatably coupled to the configurable arm, a second pulley rotatably coupled to the configurable arm, a spring, and a tension element coupled to the spring and wrapped at least partially around the first pulley and the second pulley. The method includes moving the configurable arm away from the base element and along a shaft in a direction along the axis and perpendicular to a plane of rotation of the configurable arm, rotating the configurable arm about the axis to a rotated orientation, moving the configurable arm at the rotated orientation toward the base element along the shaft to engage the configurable arm with the base element, and engaging the attachment mechanism to secure attachment of the configurable arm with the base element at a second orientation of the arm about the axis. When the configurable arm at the first orientation, the counterbalance mechanism counterbalances a load having a center of gravity located on a first side of the counterbalance mechanism, and when the configurable arm is at the second orientation, the counterbalance mechanism counterbalances the load having the center of gravity located on a second side of the counterbalance mechanism opposite to the first side.

In various implementations of the method, a third axis intersects a first axis of rotation of the first pulley, a second axis of rotation of the second pulley, and the center of gravity of the load. In some implementations, rotating the configurable arm about the axis to the rotated orientation includes rotating the configurable arm to a stopped orientation against a stop member provided in a range of motion of the configurable arm, the stopped orientation aligning or approximately aligning the configurable arm to the second orientation. In some implementations, a first slot and a second slot are provided in the base element, a tapered member is provided on the configurable arm, the first slot provided at the first orientation, and the second slot provided at the second orientation; moving the configurable arm away from base element along the shaft causes the tapered member of the configurable arm to disengage from the first slot of the base element; and the method includes providing a precise alignment of the configurable arm to the second orientation by moving the configurable arm toward the base element along the shaft to cause the tapered member of the configurable arm to engage in the second slot of the base element at the second orientation. In some implementations, the load includes a mechanical linkage coupled to the base element, and the counterbalance mechanism is included in a component of a teleoperated surgical system.

In some implementations, a counterbalance apparatus includes a spring, a tension element including a first end coupled to the spring and a second end coupled to a mechanical ground, a first pulley rotatably coupled to a rotatable member of a load and rotatable about a first axis, a second pulley rotatably coupled to the rotatable member of the load and rotatable about a second axis parallel to and offset from the first axis, a curved element coupled to the mechanical ground and including a curved surface, and a third pulley rotatably coupled to the curved element and rotatable about a third axis nonparallel to the first axis and the second axis. The tension element is at least partially wrapped around the first pulley and the second pulley, and is at least partially wrapped around the third pulley prior to being wrapped around the first pulley in a path from the first end to the second end of the tension element. In the path from the first end to the second end of the tension element, the tension element is at least partially wrapped around the curved element prior to being coupled to the mechanical ground at the second end of the tension element. Along the path from the first end to the second end of the tension element, the tension element exits contact with the third pulley and enters contact with the curved element at points located within a plane that includes the first pulley and the second pulley.

Various implementations and examples of the apparatus are described. In some implementations, the third axis of rotation extends at a non-orthogonal angle with reference to the plane, and the plane is orthogonal to the first axis and the second axis. In some implementations, the first axis and the second axis are arranged along an axis that intersects a center of gravity of the load of the counterbalance apparatus. In some implementations, the curved element is a cylindrical element that is rigidly coupled to the mechanical ground, centered on the third axis, and positioned between the third pulley and the mechanical ground, the curved surface of the curved element having a radius equal to a radius of the third pulley. In some implementations, the counterbalance apparatus further includes a fourth pulley rotatably coupled to the mechanical ground and rotatable about a fourth axis, wherein the tension element is wrapped at least partially around the fourth pulley prior to being wrapped around the third pulley in the path from the first end to the second end of the tension element, and the fourth axis is nonparallel to the first axis, the second axis, and the third axis. In some implementations, the second pulley is coupled to a base element that is rotatable about the first axis, the second pulley is orbitable about the first axis, the base element is rigidly coupled to a load, and the load includes at least a portion of a mechanical arm. In some implementations, the counterbalance apparatus further includes a configurable arm having first and second portions, the configurable arm has a first configuration orientation and a second configuration orientation, the configurable arm is rotatably coupled to the base element at the first portion of the configurable arm and is rotatable about the first axis to the first configuration orientation and to the second configuration orientation, and the configurable arm has a length aligned with an axis intersecting a center of gravity of a load coupled to the base element.

BRIEF DESCRIPTION OF THE DRAWINGS

FIGS. 9A, 9B, and 9C are front, side cross-sectional, and perspective views, respectively, of an example configurable arm that can be used in the counterbalance mechanism of FIGS. 5-7B, according to some implementations;

FIG. 15 is a flow diagram illustrating an example method to configure a counterbalance mechanism, according to some implementations;

DETAILED DESCRIPTION

Figure 1:
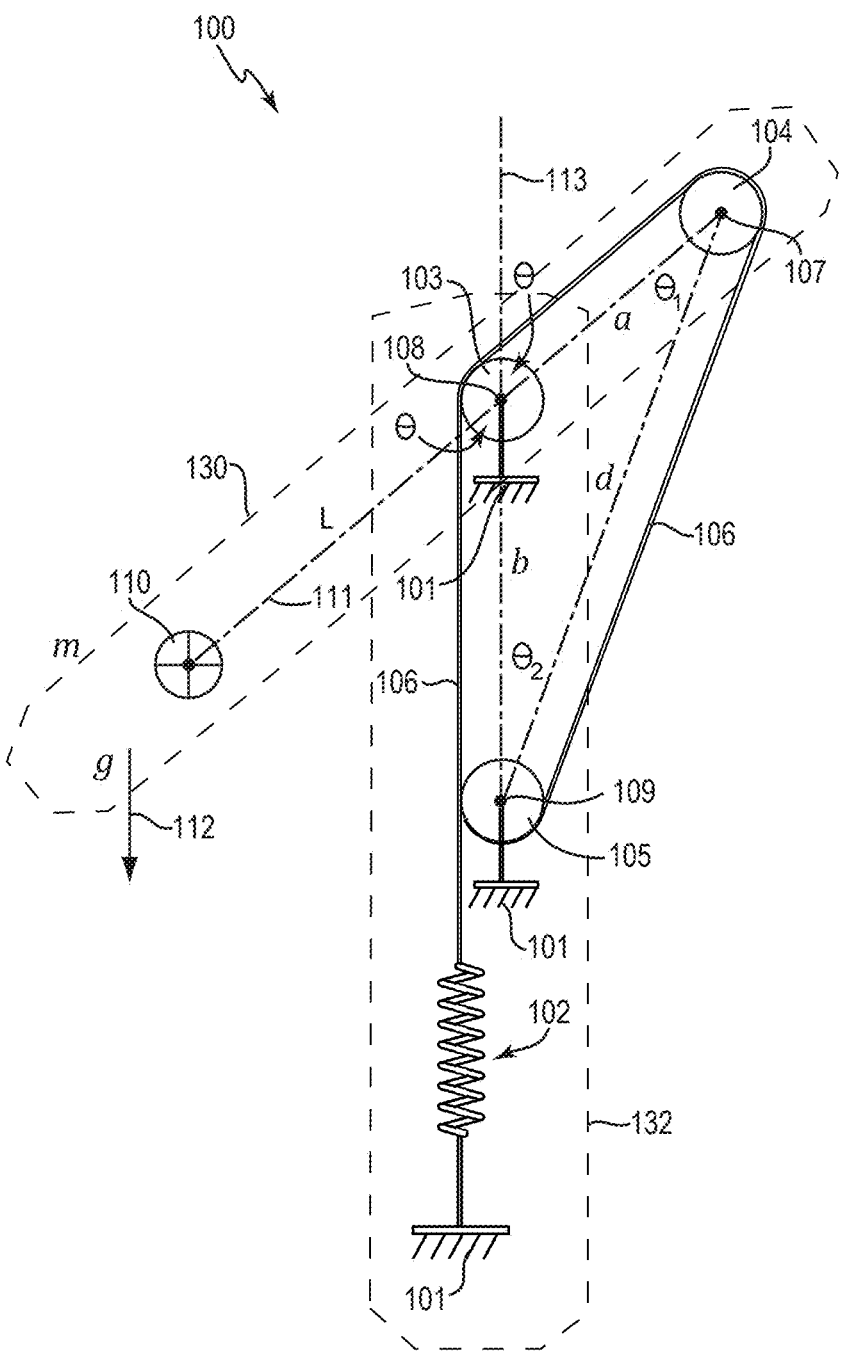
FIG. 1 is a schematic illustration of an example counterbalance mechanism that can include one or more features of the present disclosure, according to some implementations.

Implementations described herein relate to a configurable counterbalance mechanism. In some implementations of a counterbalance mechanism, a first end of a tension element (e.g., a cable) is coupled to a spring and a second end is coupled to a mechanical ground. A base element is coupled to a load and a configurable arm is rotatably coupled to the base element. A first pulley is rotatably coupled to a first portion of the configurable arm and is rotatable about a first axis. A second pulley is rotatably coupled to a second portion of the configurable arm and is rotatable about a second axis and orbitable about the first axis. The tension element is at least partially wrapped around the first pulley and the second pulley. The configurable arm is rotatably configurable about the first axis at one of a first orientation and a second orientation. The first orientation is associated with a center of gravity of the load located on a first side of the counterbalance mechanism, and the second orientation is associated with the center of gravity of the load located on a second side of the counterbalance mechanism opposite to the first side. Thus, the load center of gravity can be located to either side of the counterbalance mechanism and the counterbalance mechanism is configured to counterbalance the load positioned at the selected side.

Various features of the counterbalance mechanism are disclosed. For example, the counterbalance mechanism can include a third pulley rotatably coupled to the mechanical ground, the tension element being wrapped at least partially around the third pulley. In some implementations, the base element can be a joint gear. In some implementations, the base element can include a first slot and a second slot, where the configurable arm engages with the first slot at the first orientation and engages with the second slot at the second orientation. For example, the configurable arm can include a plug portion that includes tapered sides that are engageable with tapered sides of the slots of the base element, such that the tapered sides precisely guide the configurable arm into a slot.

A stop member can be associated with each configuration orientation, being located in the path of rotation of the configurable arm and stopping the rotation of the configurable arm such that it is aligned or approximately aligned with a targeted configuration orientation. The counterbalance mechanism can include a grounded guide pulley that guides the tension element to the spring.

In some described implementations, a counterbalance mechanism includes active portions of a tension element that are located within a single plane. For example, the third pulley can be rotatably coupled to a curved element that is coupled to ground. The third pulley can be rotatable about a third pulley axis that is angled such that, in a path from a first end to a second end of the tension element, the tension element exits contact with the third pulley and enters contact with the curved surface of the curved element at points located within a single plane that includes the first pulley and the second pulley.

Described configuration features allow a counterbalance mechanism to be quickly and easily reconfigured based on a location of a center of gravity of the counterbalanced load. For example, in some systems a left- or right-handed counterbalanced control input device may be changed to the other handedness in which the center of gravity of the control input device is flipped to the opposite side of the counterbalance mechanism. A counterbalance arm of the counterbalance mechanism can be quickly rotated from one configuration orientation to another configuration orientation as needed to balance the load on a particular side of the counterbalance mechanism. Features such as a configuration slot that receives a plug portion of the configurable arm, and tapered sides of both slot and arm, assist and guide the disengagement, rotation, and engagement of the configurable arm to a new configuration orientation. Stop members in the range of rotation of the configurable arm prevent rotation of the configurable arm past a target configuration orientation and assist guiding the arm to a new orientation.

These features provide simple and quick reconfiguration for a counterbalance mechanism that can be used to balance a load that has a center of gravity that can change its location (e.g., position or orientation) with respect to the counterbalance mechanism. For example, a load that is a control input device can be rotated 180 degrees from a left-handed configuration to a right-handed configuration, or vice versa, which can change the center of gravity of this load. Such a change in center of gravity can be counterbalanced using the counterbalance mechanism and reconfiguration procedure described herein.

Furthermore, one or more described configuration features can balance a load's center of gravity that is located far from the vertical axis of the counterbalance mechanism without requiring a large volume to change locations of components of the mechanism. For example, the described configurable arm can be rotated about a joint without requiring large shifting of components and a large housing or packaging to accommodate such shifting. Another advantage of some described implementations is that the counterbalance mechanism provides the same amount of compensation for gravity to a load in all configurations, unlike previous designs that move components such as a lower pulley for different configurations, thereby causing different amounts of cable tension and thus different amount of counterbalancing in the different configurations.

Described features allow easier production, distribution, and assembly of control input device assemblies that are provided in a single type of configuration (e.g., for left hand or for right hand), which can be easily changed to a desired configuration at an operating site.

In addition, some described implementations can provide active counterbalance elements in a single plane. This allows a counterbalance mechanism to provide counterbalance forces that more accurately reduce or cancel gravity forces on a load. In addition, this feature can provide reduced friction between a tension element (such as a cable) and one or more pulleys. In a counterbalance mechanism that includes a tension element (e.g., a cable) wrapped around multiple pulleys, one or more of the pulleys can be angled such that active portions of the tension element are located within a single plane. This allows a sinusoidal force to be produced to accurately counterbalance gravity forces on the load at all possible rotational angles of the load. In contrast, previous implementations placed the active portions of the tension element in multiple planes, such that the counterbalance mechanism did not produce force to fully cancel the gravity force on the load at all rotational angles of the load. Furthermore, the described features can produce less friction due to the tension element being wrapped around pulleys within a single plane, thus reducing contact of the tension element with the sides of grooves at the circumferences of the pulleys. Such described features allow more accurate counterbalancing of a load and thus greater consistency in user manipulation of a counterbalanced control input device and in transmission of forces to that device.

The terms "center," "parallel," "perpendicular," "orthogonal," "aligned," or particular measurements in degrees, Hertz, or other units as used herein need not be exact and can include typical engineering tolerances. Some implementations herein may relate to various objects in terms of their state in three-dimensional space. As used herein, the term "position" refers to the location of an object or a portion of an object in a three dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw around the Cartesian X, Y, and Z axes). As used herein, the term "pose" refers to the position of an object or a portion of an object in at least one degree of translational freedom and to the orientation of that object or portion of the object in at least one degree of rotational freedom (up to six total degrees of freedom).

As referred to herein, a mechanically grounded member is constrained with respect to possible position and orientation motion in a working environment (e.g., an operating area or room). Such a unit is kinematically coupled to a mechanical ground (e.g., mechanically connected to ground directly or indirectly). As used herein, the term "proximal" refers to an element that is close to (or closer to) a mechanical ground and the term "distal" refers to an element that is away from (or further from) a mechanical ground. The term "torque" as used herein refers to rotational forces and/or refers to a context of rotational motion, and in various implementations using one or more described features, other types of forces can be used as appropriate in place of or in addition to torque, e.g., linear forces or other forces, and/or forces in a context of translational motion.

FIG. 1 is a schematic illustration of an example counterbalance mechanism 100 that can include one or more features of the present disclosure, according to some implementations. Counterbalance mechanism 100 can be used to provide counterbalance forces to a load, e.g., a load such as a rotating member of a mechanical arm, to counter (e.g., cancel or reduce) gravitational forces on the load. The sizes and lengths of components and distances between components shown in FIG. 1 are not actual dimensions, but rather schematic examples shown for simplicity. Portions shown in dashed lines are representations of components that are part of a system to which the counterbalance mechanism 100 is connected.

Counterbalance mechanism 100 is coupled to a load that is counter balanced against gravity. In this example, the load includes a rotatable member 130, indicated by dashed lines in FIG. 1. Rotatable member 130 can have a variety of different dimensions, shapes, etc. In some examples, as shown, rotatable member 130 is coupled by a rotary joint to a grounded member 132, indicated by dashed lines in FIG. 1. Rotatable member 130 is rotatable about axis 108 with reference to grounded member 132. Grounded member 132 can be a mechanical ground 101 with respect to the counterbalance mechanism 100. Grounded member 132 can have a variety of different dimensions, shapes, etc. In some implementations, counterbalance mechanism 100 is provided between rotatable member 130 and grounded member 132.

In some implementations, rotatable member 130 and grounded member 132 are included in a mechanical arm, e.g., as links in the linkage of a mechanical arm. In some implementations, grounded member 132 can be coupled to another member, e.g., another link of the mechanical arm. In some example implementations, the mechanical arm can be used in a user control system, e.g., the arm can be coupled to a control input device that can be manipulated by a user in one or more degrees of freedom. In some example implementations, the mechanical arm can be used as a manipulator arm in a manipulator device or controlled device operating at a worksite, and movement of the manipulator arm is controlled by a user that is correspondingly manipulating a control input device associated with the manipulator arm. Some examples of the manipulator arm are described below. In various other implementations, the mechanical arm is used in other applications.

Counterbalance mechanism 100 includes a counterbalance spring 102 and counterbalance pulleys 103, 104, and 105. A tension element 106 is coupled to spring 102 and wraps around pulleys 103, 104, and 105.

Spring 102 is coupled to a mechanical ground 101 at a first end of the spring. A second end of spring 102 is coupled to a first end of a tension element 106. Spring 102 provides a spring force on tension element 106. Spring 102 has a spring constant k. Spring 102 can be used as a tension spring, as shown, or alternatively as a compression spring in which, for example, tension element 106 is coupled to the first end of the spring and passes through the spring, such that a load causes the spring to be compressed.

Tension element 106, and any of the other tension elements described in the various implementations herein, can be any flexible element that can be routed to and contacts (e.g., wraps at least partially around) the components of the counterbalance mechanisms described herein. For example, one or more tension elements can be a flexible tension element, e.g., a steel tension element. In some implementations, the tension elements are cables. In some implementations, one or more of the tension elements can be belt, chains, or other flexible elements. The tension elements described herein transmit force from one component to another, e.g., from a spring to a load (e.g., via pulley(s)).

Tension element 106 is routed from its first end at spring 102 toward a counterbalance pulley system, where it wraps at least partially against or around pulley 105, and at least partially around pulleys 103 and 104. After pulley 104, tension element 106 is wrapped at least partially around a curved element (e.g., cylindrical feature) (not shown) that is adjacent to pulley 105 and fixed to the mechanical ground.

Tension element 106 is anchored at its second end (e.g., at an opposite end to the first end of tension element 106) to mechanical ground, e.g., at the grounded curved element adjacent to pulley 105 or otherwise to grounded member 132. In various implementations, tension element 160 can be wrapped around the curved element by a different amount depending on the implementation, e.g., depending on the range of motion of rotating member 130.

In some examples, from its first end at spring 102, tension element 160 wraps partially around pulley 105. In some implementations, pulley 105 is rotatably coupled to ground member 132. In some implementations, as described below with reference to FIG. 13, pulley 105 has the same radius as counterbalance pulleys 103 and 104 and is angled such that its axis of rotation 109 is nonparallel to the axis of rotation 108 of the first pulley 103 and axis of rotation 107 of the second pulley 104.

Pulley 103 is rotationally coupled to a member, which in this example is rotatable member 130 (e.g., link) of the mechanical arm, and has axis of rotation 108 that is coaxial with a joint axis of the rotatable member 130 of the mechanical arm. Pulley 104 is rotationally coupled to rotatable member 130 and rotates about an axis of rotation 107. Pulley 104 is at a location that is offset from axis 108 orbits or swings about axis 108 and pulley 103 with member 130 as member 130 rotates about axis 108. Member 130 has a mass m and a center of gravity 110 that is on the opposite side of axis 108 from the pulley 104. The axis of rotation 107 is located in a line with center of gravity 110 and axis of rotation 108, e.g., an axis 111 intersects the center of gravity 110, axis of rotation 108, and axis of rotation 107. In some implementations, as described below with respect to FIGS. 4-12, pulleys 103 and 104 can be rotatably coupled to a configurable arm that can be reconfigured based on a location of the center of gravity 110 with respect to the counterbalance mechanism, e.g., with respect to vertical axis 113.

After pulley 104 toward its second end, tension element 160 wraps around the curved element adjacent to pulley 105 (e.g., positioned behind pulley 105 in FIG. 1). In some implementations, the curved element is a cylindrical feature that is fixed to mechanical ground 101, e.g., rigidly coupled to grounded member 132. The curved element can have the same radius as pulley 105 and can have a center axis that is coincident with (e.g., the same as) rotational axis 109 of pulley 105. In some other implementations, the curved element is not cylindrical and has a different shape, or is an element that is a feature or portion of grounded member 132. For example, the curved element can be a feature on the grounded member 132 that that has a curved surface that is a portion of a cylinder that has the same radius as pulley 105. An example of an implementation of the curved element is shown with respect to FIG. 14.

In some implementations, one or more of the pulleys of the counterbalance mechanism 100 (or of any of the counterbalance mechanisms described herein) can include grooves and/or flanges on their circumferential surface to guide and support a tension element thereon, e.g., to cause an engaged tension element to be securely wrapped around the pulley, to stay in place around the pulley, and/or to prevent the tension element from drifting toward an edge of the pulley during pulley rotation.

In operation, rotatable member 130 can rotate about axis 108. Spring 102 provides a counterbalance force on rotatable member 130 via tension element 106 in opposition to the force of gravity 112 being exerted on the rotatable member 130. For example, spring 102 provides a force on tension element 106 which resists the orbiting motion of pulley 104 about the axis 108 caused by rotation of rotatable member 130, thus providing a counterbalance force on rotatable member 130 that opposes gravitational force on the rotatable member. For example, if the counterbalance mechanism is detached from the rotatable member 130, center of mass 110 would come to a rest at the 6 o'clock position about axis 108. In some example implementations, this application of counterbalance forces allows reduced force magnitudes to be output from actuators (e.g., motors) to move or support the rotatable member 130 against gravity as compared to implementations that do not provide such counterbalance forces.

As shown in FIG. 1, an angle θ is denoted between the current orientation of pulley 104 and an orientation of the pulley 104 that would cause the pulleys 103, 104, and 105 to be aligned, e.g., their centers intersected by a single line. In FIG. 1, the aligned orientation is along the vertical line 113. This same angle θ exists between the center of mass 110 and its stable equilibrium position along vertical line 113.

Parameters of the counterbalance mechanism 100 include distances between components of the mechanism 100 and/or rotatable member 130. One parameter is a, the planar distance between axis of rotation 108 and the axis of rotation 107 of pulley 104. Another parameter is b, the planar distance between axis of rotation 108 and the axis of rotation 109 of pulley 105. The distance between the axis 109 and the axis 107 is d, which is a function of the selected parameters a and b and the angle θ. For example, since pulley 104 rotates with rotatable member 130, distance d varies and is a function of a, b, and angle θ at which the rotatable member is currently oriented. The planar distance of center of mass 110 to axis of rotation 108 is L, which is a parameter of the counterbalance mechanism as a "lever arm" length of the load of the mechanism (rotatable member 130). A different rotatable member 130 (or other load) may have a different mass 110 and/or different lever arm length L. Another design parameter of the counterbalance mechanism 100 is k, the spring rate (e.g., spring constant or stiffness) of spring 102. The counter balance design parameters k, a, and b can be chosen to balance the gravity load for the given rotatable member 130 having a particular mass 110 and lever arm length L.

At any given angle θ, the mass m of the link generates a moment, $M_{grav}$, about the rotary axis 108, as indicated in Equation 1:

$$M_{grav} = m \cdot g \cdot L \cdot \sin(\theta) \tag{1}$$

where g is the gravitational acceleration.

If the tension element 106 is chosen such that the spring deflection of spring 102 is equal to the distance a+b when θ is zero, the moment generated by the counterbalance mechanism, $M_{cb}$, about the rotary axis 108 is as shown in Equation 2:

$$M_{cb} = -k \cdot a \cdot b \cdot \sin(\theta) \tag{2}$$

where k is the spring constant of spring 102.

Balancing the gravity load of the rotatable member 130 can be performed by matching the product of the three parameters k, a, and b to the gravity load, e.g., $M_{grav} - M_{cb} = 0$ for all angles θ. By matching the product of k, a, and b with the parameter product of m, g, and L, the counterbalance mechanism can balance the gravity load of the rotatable member 130. As rotating member 130 rotates, the counterbalance mechanism produces a sinusoidal, periodic torque that cancels the gravity torque; e.g., force applied to the rotating member is dynamically adjusted to compensate for gravity as applied during the rotation.

Figures 2, 3:
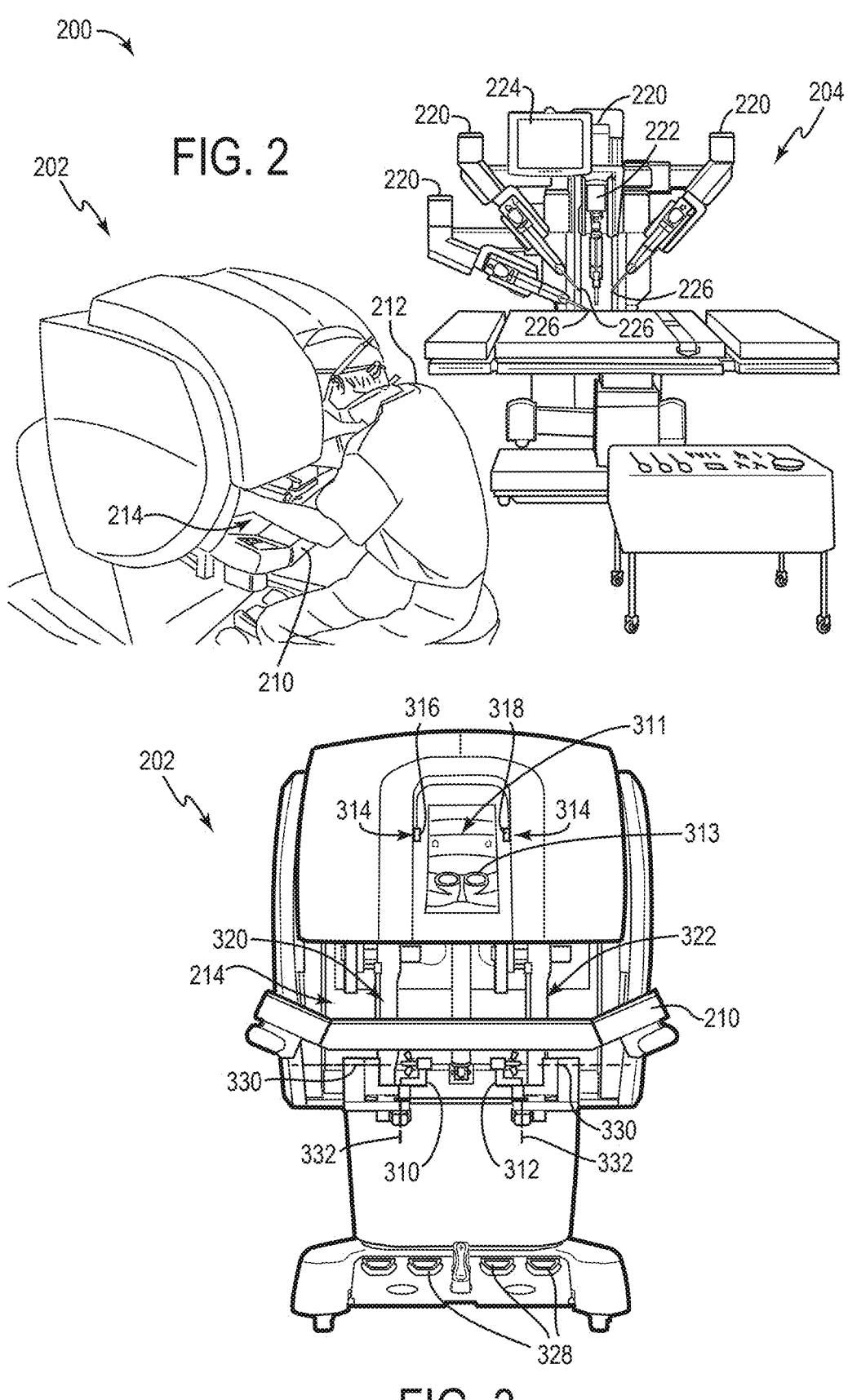
FIG. 2 is a diagrammatic illustration of an example implementation of a teleoperated surgical system which can be used with one or more features disclosed herein, according to some implementations.
FIG. 3 is a front elevational view of an example user control system as shown in FIG. 2, according to some implementations.

FIG. 2 is a diagrammatic illustration of an example teleoperated surgical system 200 which can be used with one or more features disclosed herein. Other types of control systems, teleoperated systems, or master-slave systems can be used in various implementations including one or more described features. Teleoperated surgical system 200 includes a user control system (e.g., surgeon's console) 202 and a manipulator system 204.

In this example, the user control system 202 includes a viewer 313 (shown in FIG. 3) where an image of a worksite is displayed during an operating procedure using the system 200. For example, the image can be displayed by a display device, such as one or more display screens, to depict a surgical site during a surgical procedure. A support 210 is provided on which a user 212, e.g., an operator such as a surgeon, can rest forearms while gripping control input devices, such as control input devices 310 and 312 shown in FIG. 3. The control input devices 310 and 312 are positioned in a workspace 214 disposed inwardly beyond the support 210. When using the user control system 202, the user 212 can sit in a chair in front of the control system 202, position the user's head/eyes in front of the viewer 313, and grip the control input devices 310 and 312, one in each hand, while resting forearms on the support 210. In some implementations of control system 202 and/or control input devices 310 and 312, the user can stand while operating the control input devices.

A manipulator system 204 is also included in the teleoperated system 200. For example, manipulator system 204 can be any type of device controlled by a user control device or control input device. In some implementations as shown, during a surgical procedure, the manipulator system 204 can be positioned close to a surgical site located with reference to a patient or model disposed on an operating table or other type of worksite). In various implementations, manipulator system 204 can remain stationary until a particular procedure or stage of a procedure is completed, or can move relative to a work site. Manipulator system 204 can include one or more manipulator devices that can include manipulator arm assemblies 220. In some examples, an arm assembly 220 can include multiple links rotatably coupled to each other. Portions of the arm assembly 220 can be actuated with a motor and sensed about rotational axes. In some examples, one or more of the arm assemblies 220 can be configured to hold a manipulator device such as an image capturing device, e.g., an endoscope 222, which can provide captured images of a portion of the surgical site. In some implementations, the captured images can be transmitted to the viewer 313 of the user control system 202 and/or transmitted to one or more other displays, e.g., a display 224 coupled to the manipulator system 204.

In some examples, each of the other arm assemblies 220 may include a manipulator device such as a surgical tool 226. Each surgical tool 226 can include a surgical end effector, e.g., for treating tissue of the patient. For example, an end effector can include one or more motors or other actuators that operate associated features of the end effector, such as the pitch, yaw, and/or roll of the end effector, opening jaws or moving a blade of the end effector, the output of material transported through a connecting tube (e.g., liquid or other fluids), suction forces, and/or any of a multiple of other end effector functions. End effector mechanisms can include flexible elements, articulated "snake" arms, steerable guide tubes, catheters, scalpel or cutting blade, electrical instruments, scissors, forceps, retractors, dilators, clamps, cauterizing tools, needles, staplers, drills, probes, scopes, light sources, guides, measurement devices, vessel sealers, laparoscopic tools, and/or other tip, mechanism or device. One example of a surgical manipulator arm is a da Vinci® surgical system instrument manipulator arm in surgical systems commercialized by Intuitive Surgical, Inc. of Sunnyvale, California.

In this example, the arm assemblies 220 can be caused to move and articulate the surgical tools 226 in response to manipulation of corresponding control input devices, e.g., control input devices 310 and 312 at the user control system 202 by the user 212. This arrangement allows user 212 to, for example, direct surgical procedures at internal surgical sites through minimally invasive surgical apertures. For example, one or more actuators coupled to the arm assemblies 220 can output forces to cause links or other portions of the arm assemblies to move in particular degrees of freedom in response to control signals received from the user control system 202. For example, movement of an arm and end effector in one or more degrees of freedom can correspond to movement in one or more degrees of freedom of an associated control input device handle 310 or 312 by a user. The user control system 202 can be used within a physical environment (e.g., an operating room) with the manipulator system 104 or can be positioned more remotely from the manipulator system 202, e.g., at a different location than manipulator system 204.

Some implementations of teleoperated system 200 can provide different modes of operation. In some examples, in a non-controlling mode (e.g., safe mode) of teleoperated system 200, the controlled motion of manipulator system 204 is disconnected from the control input devices of user control system 202, such that movement and other manipulation of the control input devices does not cause motion of manipulator system 204. In a controlling mode of teleoperated system 100 (e.g., following mode, in which one or more controlled manipulators follow a corresponding control input device), motion of manipulator system 104 can be controlled by control input devices 310 and 312 of the user control system 202 such that movement and other manipulation of control input devices 310 and 312 causes motion of the manipulator system 204. The controlled functions of the manipulator device can include movement of the manipulator device. In some examples, the control input devices are provided with the same degrees of freedom as manipulator devices of the manipulator system 204 to provide the user with telepresence.

Some implementations can be or include a teleoperated medical system such as a da Vinci® Surgical System (e.g., a Model IS3000 or IS4000, marketed as the da Vinci Si® or da Vinci Xi® Surgical System), commercialized by Intuitive Surgical, Inc. of Sunnyvale, California. However, features disclosed herein may be implemented in various ways, including in implementations at least partially computer-controlled, controlled via electronic control signals, manually controlled via direct physical manipulation, etc. Implementations on da Vinci® Surgical Systems are merely exemplary and are not to be considered as limiting the scope of the features disclosed herein. For example, different types of teleoperated systems having controlled devices at work-sites can make use of features described herein. Other, non-teleoperated systems can also use one or more described features, e.g., various types of control systems and devices, peripherals, etc.

For example, in various implementations, other types of computer-assisted teleoperated systems can be used with one or more features described herein, in addition to surgical systems. Such teleoperated systems can include controlled manipulator devices of various forms. For example, submersibles, hazardous material disposal units, industrial applications, applications in hostile environments and worksites (e.g., due to weather, temperature, pressure, radiation, or other conditions), general robotics applications, and/or remote-control applications (e.g., remote controlled vehicle or device with a first-person view), may utilize teleoperated systems that include controlled devices for sensory transmission (conveyed visual, auditory, etc. experience), manipulation of work pieces or other physical tasks, etc., and may use mechanically grounded and/or ungrounded control input devices to remotely control the manipulator devices. Any such teleoperated systems can be used with the various features described herein.

In some implementations, a controlled manipulator device can be a virtual representation of device, e.g., presented in a graphical simulation provided by a computing device coupled to the teleoperated system 200. For example, a user can manipulate the control input devices 310 and 312 of the user control system 202 to control a displayed representation of an end effector in virtual space of the simulation, similarly as if the end effector were a physical object coupled to a physical manipulator device.

FIG. 3 is a front elevational view of an example user control system 202 as described above for FIG. 2. User control system 202 includes a viewer 313 that provides a display of images of a worksite during a procedure using the teleoperated system 200. The viewer 313 can be positioned within a viewing recess 311 in which the user 212 can position his or her head to view images displayed by the viewer 313. When using the user control system 202, the user 212 can sit in a chair (or stand) in front of user control system 202 and position his or her head within the recess 311 such that his or her eyes are positioned in front of the viewer 313.

In some implementations, one or more user presence sensors 314 can be positioned at one or more locations of the user control system 202 to detect the presence of a user's head located next to or near to the user control system 202. In this example, the user presence sensors 314 can sense a presence of a user's head within recess 311. For example, an electromagnetic sensor (e.g., optical sensor) can be used for a presence sensor. For example, if an emitted beam is interrupted from detection by the detector, e.g., due to the user's head blocking the beam, then the system determines that the user is in a position to use the control input devices of the user control system 202.

Two control input devices 310 and 312 are provided for user manipulation. In some implementations, each control input device 310 and 312 can be configured to control motion and functions of an associated arm assembly 220 of the manipulator system 204. For example, a control input device 310 or 312 can be moved in a plurality of degrees of freedom to move a corresponding end effector of the manipulator system 204 in corresponding degrees of freedom. The control input devices 310 and 312 are positioned in workspace 214 inwardly beyond the support 210. For example, a user 212 can rest his or her forearms while gripping the two control input devices 310 and 312, with one control input device in each hand. The user also positions the user's head within the viewing recess 311 to view the viewer 313 as described above while manipulating the control input devices 310 and 312.

Control input devices 310 and 312 may include an actuatable grip portion (e.g., handle) for actuating corresponding instruments of a manipulator system, e.g., for closing grasping jaws, applying an electrical potential to an electrode, delivering a medicinal treatment, and the like. In some implementations, a grip function, such as moving two grip portions of a control input device together and apart in a pincher movement, can provide an additional mechanical degree of freedom (i.e., a grip DOF). In some example implementations, control input devices 310 and 312 may provide control of one or more surgical instruments 226 in a surgical environment or proxy surgical instruments in a virtual environment. The control input devices may include any number of a variety of input devices manipulable by the user, such as kinematically linked (mechanically grounded) hand grips, finger grips, joysticks, trackballs, data gloves, trigger-guns, hand-operated controllers, voice recognition devices, touch screens, and the like. Some examples of input devices that can be used as control input devices 310 and 312 are described below.

In some implementations, control input devices 310 and 312 are manual input devices which can be moved in all six Cartesian degrees of freedom by a user, including motion about axes 330 and 332. Control input device 310 can be coupled to a control input arm assembly 320 that provides one or more of the degrees of freedom to the control input device, and control input device 312 can be similarly coupled to a control input arm assembly 322. For example, control input arm assembly 314 and 316 can each include a mechanical linkage that includes multiple members rotatably coupled to at least one other of the members. Some examples of a control input arm assembly are described below. In some implementations, actuators such as motors can be included in or coupled to a control input arm assembly to output forces on the control input device 310 or 312.

Some implementations of user control system 202 can include one or more foot controls 328 positioned below the control input devices 310 and 312, e.g., to input various commands to the teleoperated system while the user is operating the user control system 202.

Figure 4:
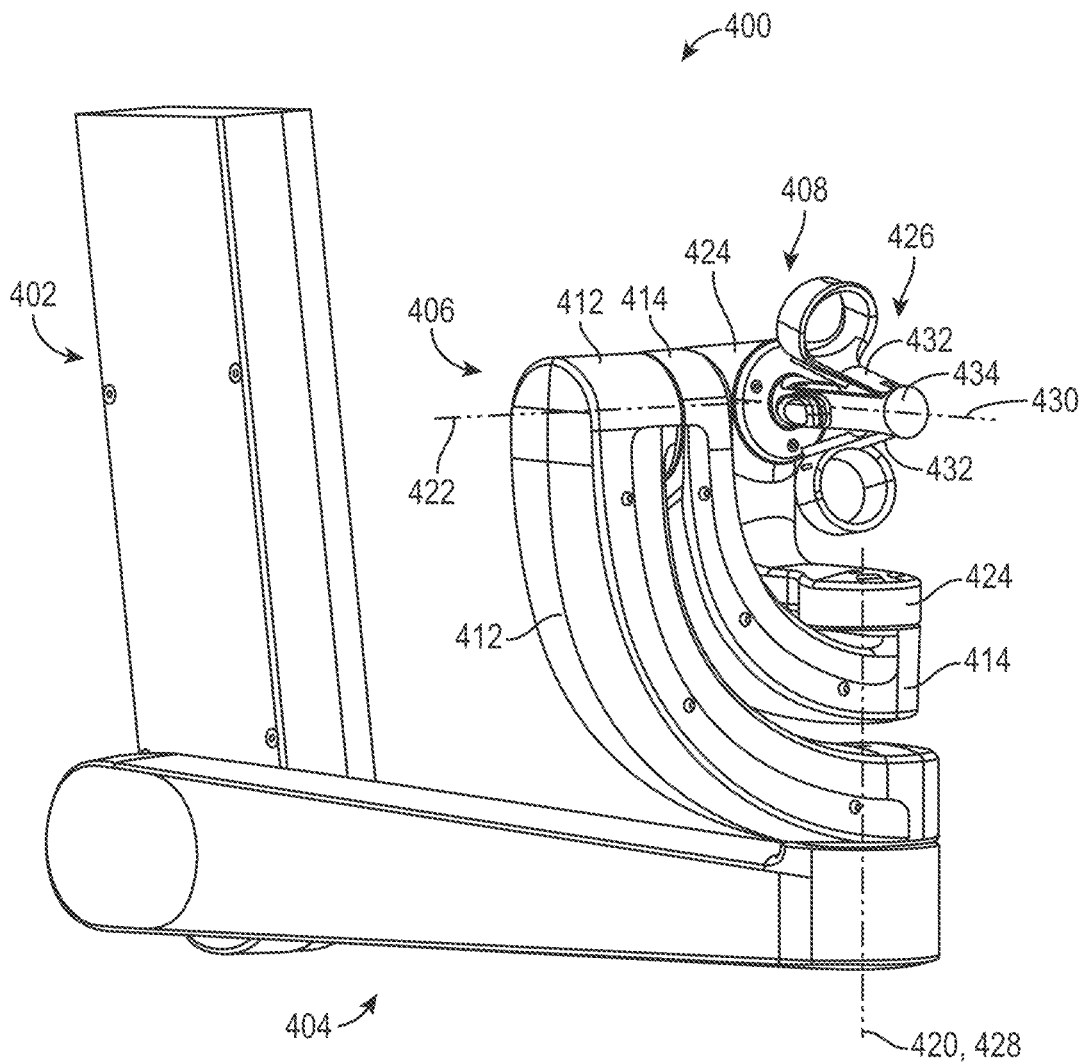
FIG. 4 is a perspective view of a portion of a control input arm assembly that includes one or more counterbalance features described herein, according to some implementations.

FIG. 4 is a perspective view of a portion of a control input arm assembly 400 that includes one or more counterbalance features described herein, according to some implementations. In some implementations, control input arm assembly 400 can be included in a user control system, e.g., assembly 400 can be control input arm assembly 320 or 322 of user control system 202 as described above in FIGS. 2 and 3. Arm assembly 400 includes a first member 402, a second member 404, a device linkage 406, and a control input device 408.

First member 402 can be coupled at a proximal portion to a mechanical ground. For example, first member 402 can be rotatably coupled to a support, housing, or other mechanically grounded component of a user control system, e.g., user control system 202 of FIG. 2. Second member 404 is rotatably coupled at a proximal portion to a distal portion of first member 402. In the configuration shown, first member 402 is approximately vertically oriented and second member 404 is approximately horizontally oriented when the assembly 400 is at rest or in a neutral, unused state.

Device linkage 406 is rotatably coupled at a proximal portion to a distal portion of second member 404. In some implementations, device linkage 406 can be a linkage of multiple members, where each member is rotatably coupled to at least one other of the members. In the described implementation, device linkage 406 includes a first link 412 and a second link 414. A proximal portion of first link 412 is rotatably coupled to a distal portion of second member 404. A proximal portion of second link 414 is rotatably coupled to a distal portion of first link 412. In some implementations as shown, first link 412 rotates about axis 420 at its rotary coupling to second member 404, and second link 414 rotates about axis 422 at its rotary coupling to first link 412, where axis 422 is orthogonal to axis 420.

Control input device 408 includes a support member 424 and a grip portion 426. Support member 424 that has a proximal portion rotatably coupled to a distal portion of second link 414. In this example, support member 424 extends horizontally and vertically in an approximate "L" shape, and grip portion 426 is rotatably coupled to a distal portion of member 424. In the described implementation, member 424 rotates about an axis 428 with respect to second link 414. Axis 428 is coincident with axis 420 in the configuration shown in FIG. 4. In some implementations, device linkage 406 forms or includes a gimbal mechanism that provides three degrees of freedom to grip portion 426. Some examples of control input device 408 are described below with reference to FIG. 16.

In some examples, grip portion 426 can be moved in a plurality of degrees of freedom, e.g., six degrees of freedom including three rotational degrees of freedom and three translational degrees of freedom. In some implementations, each degree of freedom of the grip portion 426 can control a different manipulator degree of freedom (or other motion) of an end effector of the manipulator system 204. One or more degrees of freedom can be sensed by associated sensors and/or actuated by actuators (motors, etc.) (not shown).

Various sensors can be coupled to the members, links, control input device, and/or other components of the assembly 400 and can detect the orientations and positions of these components of the assembly in their degrees of freedom. The sensors can send signals describing sensed positions and/or motions to one or more control circuits of the teleoperated system 200. In some modes or implementations, the control circuits can provide control signals to a manipulator device, e.g., manipulator system 204. For example, the orientations of the grip members 432 in their degrees of freedom can be used to control any of various degrees of freedom of an end effector of the manipulator system 204. In some examples, a position in a translational degree of freedom and/or orientation in a rotational degree of freedom can be derived from rotations of components (e.g., links of the linkage including members 402, 404, and 424 and links 412 and 414) as sensed by rotational sensors. Some implementations can include linear sensors that can directly sense translational motion of one or more components.

Various implementations of the assembly 400 can provide one or more active actuators (e.g., motors, voice coils, etc.) to output active forces on the components of assembly 400. For example, a sensor and/or actuator can be housed in a housing of control input device 408 and coupled to the grip members 432 by a transmission to output active forces on grip members 432 in their rotational degrees of freedom. Some implementations can provide one or more passive actuators (e.g., brakes) or springs between components to provide resistance in particular degrees of freedom.

In this example, first member 402 can be oriented approximately vertically and second member 404 can be oriented approximately horizontally as shown in FIG. 4 when in a non-operating state. First link 412, second link 414, and member 424 can be oriented such that first link 412 and second link 414 are to the left of control input device 408 and to the left of a user's hand operating the control input device 408, in the view of FIG. 4. These members can be rotated to other orientations when the control input device 408 is moved in space, e.g., by a user. For example, the user's left hand can grasp control input device 408 and move control input device 408 in space, such that the links 412 and 414 and members 404 and 402 move to accommodate the motion of the control input device 408. Rotational sensors, e.g., within each rotary coupling between the members and links, can measure the rotation of each link and member such that the position, orientation, and motion of the control input device 408 is determined during user manipulation of control input device 408.

In the described implementation, a counterbalance mechanism is coupled between first link 412 and second link 414 which counterbalances the force of gravity exerted on the mass that is rotatably coupled to the distal portion of first link 412. That mass includes second link 414 and control input device 408. The center of gravity of this mass extends away from axis 422, first link 412, and second link 414 to the rear in the view shown in FIG. 4. This is due to the horizontal portion of member 424 extending in the rearward direction. This center of gravity is positioned such that gravity exerts a downward force on control input device 408 and link 414 if these components are moved upward by the user in either rotational direction about axis 422 in the view shown in FIG. 4. The counterbalance mechanism opposes this downward gravity force. This allows the control input device 408 and link 414 to be moved with less required force from the orientation shown in FIG. 4 about axis 422, e.g., creating easier movement of these components by the hand of the user and/or by actuators of the assembly 400.

In an example scenario, arm assembly 400 is one of two control input assemblies installed in a user control system, such as control input arm assemblies 320 and 322 of user control system 202 in FIG. 3. Control input arm assembly 400 is configured to be positioned at the left side of a user hand workspace such as workspace 214 for use with the user's left hand, e.g., the user's left hand is to grip the control input device 408 similarly to control input device 310 of FIG. 3.

In this scenario, arm assembly 400 has been installed at the right side of workspace 214 and thus should be used with the user's right hand, e.g., the user's right hand is to grip the control input device 408 similarly to control input device 312 of FIG. 3. In some examples, arm assembly 400 and all similar arm assemblies may have been received from a manufacturer or seller in the left-hand configuration, which allows production and/or assembly costs of the arm assembly to be reduced. In this example, arm assembly 400 is installed in the right-hand location of user control system 202, and is to be reconfigured from left-handed use to right-handed use. This reconfiguration includes configuring the counterbalance mechanism that is located between first link 412 and second link 414, as described in greater detail below.

Figure 5:
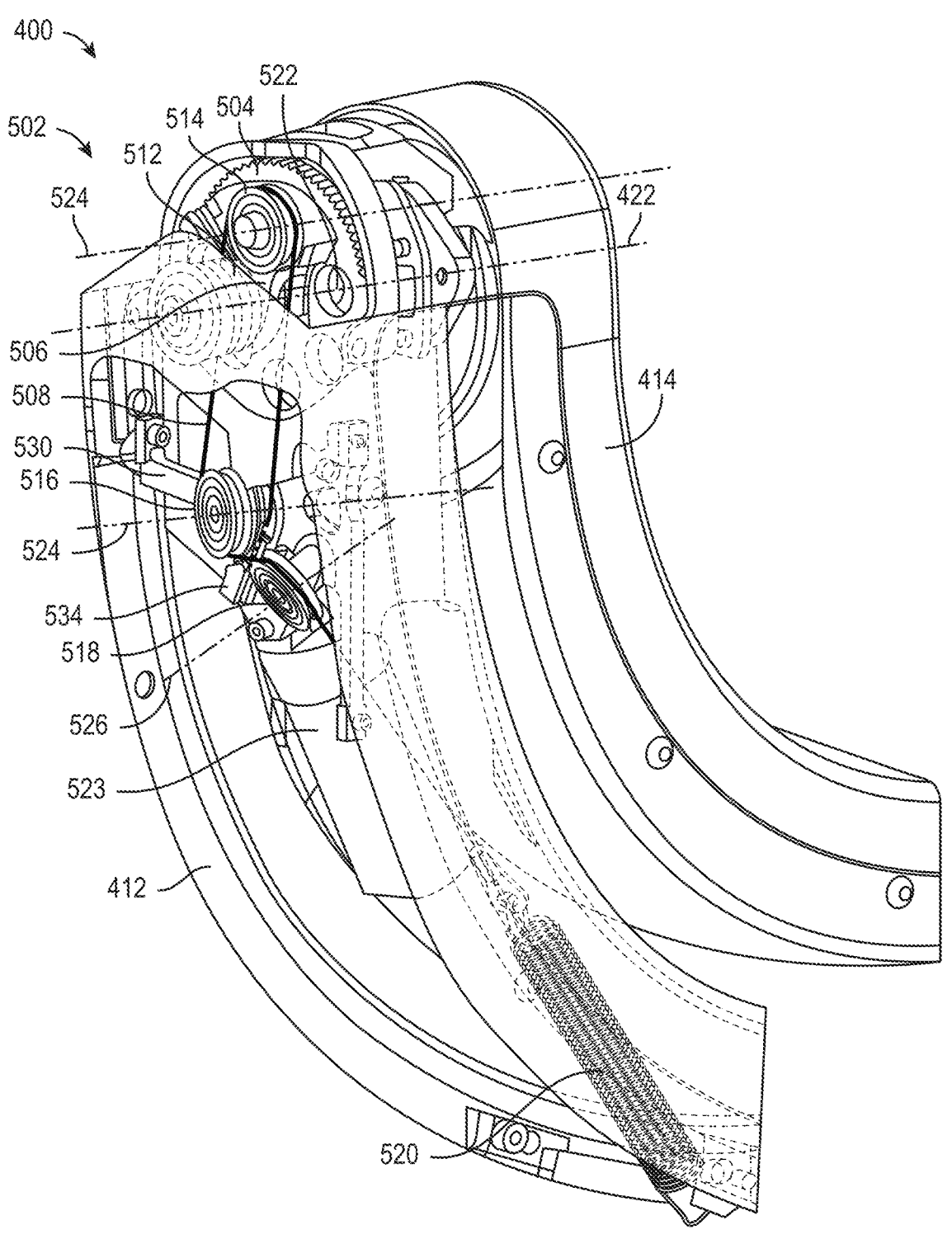
FIG. 5 is a perspective view of a portion of the interior of a link of the control input arm assembly of FIG. 4, according to some implementations.
Figure 6:
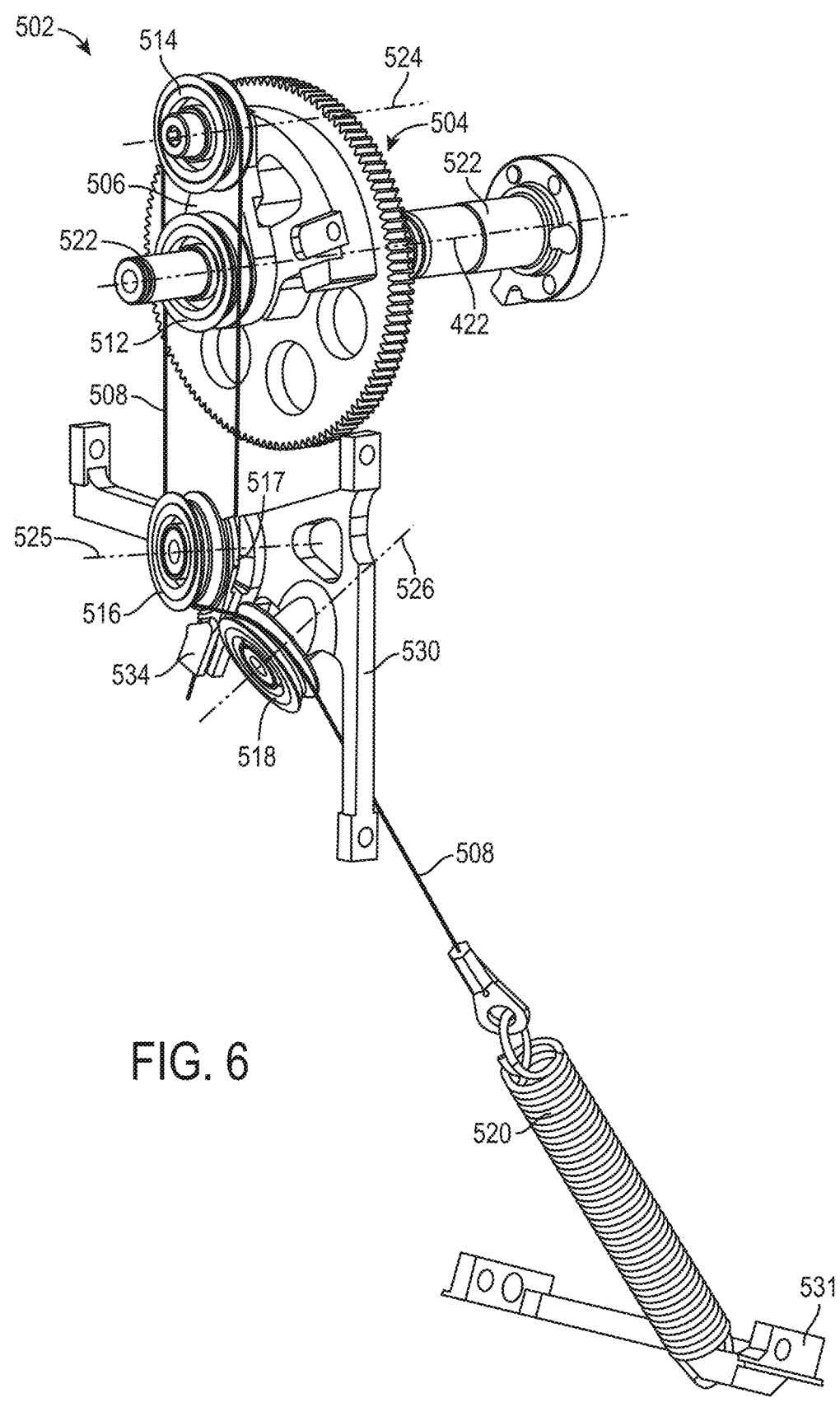
FIG. 6 is a perspective view of the counterbalance mechanism without other portions of first link shown in FIG. 5, according to some implementations.

FIGS. 5 and 6 are perspective views showing a counterbalance mechanism 502 that can be used in the control input device arm assembly of FIG. 4, according to some implementations. FIG. 5 shows a portion of links 412 and 414 of control input arm assembly 400, according to some implementations, where an interior portion of link 412 and the counterbalance mechanism 502 are exposed to view. FIG. 6 shows the counterbalance mechanism 502 of FIG. 5 without the surrounding link portions.

In some examples, a portion of the housing of first link 412 of device linkage 406 can be removed in preparation of reconfiguring the counterbalance mechanism 502 for right-handed use. For example, screws that hold the cover in place can be removed and a cover lifted from the first link 412.

The interior of first link 412 includes counterbalance mechanism 502. Counterbalance mechanism 502 includes a joint gear 504, a configurable arm 506, a tension element 508, multiple counterbalance pulleys including first pulley 512, second pulley 514, and third pulley 516, a curved element 517, a guide pulley 518, and a counterbalance spring 520.

Joint gear 504 is a base element of counterbalance mechanism 502 and can be rigidly coupled to a shaft 522 that is in turn rigidly coupled to second link 414. Joint gear 504 and shaft 522 are rotatable with respect to first link 412. Joint gear 504, shaft 522, and second link 414 thus rotate as a unit about axis 422 with respect to first link 412. In some implementations, joint gear 504 can include multiple gear teeth on its circumferential surface which engage other gear teeth of one or more gears coupled to an actuator 523 (e.g., motor) and/or sensor (e.g., optical encoder or other sensor that senses rotation of a shaft). In other implementations, a different base element can be used in counterbalance mechanism 502 instead of joint gear 504, e.g., a plate, cylinder, rectangular element, or other element that can engage configurable arm 506 similarly as described herein.

Configurable arm 506 includes a first portion and second portion, and is rotatably coupled to shaft 522 at the first portion (e.g., first end), and thus is rotatably coupled to joint gear 504. Configurable arm 506 provides a rigid link between first counterbalance pulley 512 and second counterbalance pulley 514. The second portion (e.g., second end) of configurable arm 506 is detachably coupled to joint gear 504 via an attachment mechanism (e.g., screw or pin in an aperture, or other attachment mechanism) as described in greater detail below. Configurable arm 506 is located adjacent to joint gear 504 and its second portion is secured to joint gear 504 during operation of the counterbalance mechanism. Configurable arm 506 can be configured to a different orientation to provide a different configuration of the counterbalance mechanism, as described in greater detail with respect to FIGS. 7A-11D.

First pulley 512 is rotatably coupled to the first portion (e.g., first end) of configurable arm 506 at axis 422. First pulley 512 is rotatable about axis 422 as its axis of rotation. First pulley 512 is rotatably coupled to a mechanical ground via configurable arm 506 and shaft 522.

Second pulley 514 is rotatably coupled to the second portion (e.g., second end) of configurable arm 506 and rotates about an axis 524, where axis 524 is parallel to axis 422 and is located offset from axis 422 by a particular distance, e.g., distance a shown in FIG. 1. Thus, if configurable arm 506 is rotated about axis 422, second pulley 514 orbits axis 422. In some examples, second pulley 514 is rotatably coupled to an end of configurable arm 506.

Third pulley 516 is rotatably coupled to first link 412, which acts as a mechanical ground to the counterbalance mechanism. For example, third pulley 516 can be rotatably coupled to a frame portion 530 of first link 412. Third pulley 516 rotates about an axis 525, which is located approximately below the first pulley 512 as shown in FIGS. 5 and 6.

A curved element 517 is rigidly coupled to mechanical ground (e.g., to frame portion 530) and is positioned adjacent to third pulley 516. In some implementations, curved element 517 can be a cylindrical feature (or a partially cylindrical feature) that has a curved surface with the same radius as pulley 516 and a center axis coincident with the rotational axis 525 of third pulley 516. In some implementations, as shown in FIG. 6, curved element 517 includes a curved surface around which tension element 508 can be wrapped, and can include a groove through which the tension element 508 is routed toward a grounded element 534. In various implementations, curved element 517 can be a feature having a different shape or is an element that is a portion of frame portion 530 or first link 412.

Guide pulley 518 is rotatably coupled to first link 412, e.g., to frame portion 530 of first link 412. Guide pulley 518 rotates about an axis 526, which in this example is nonparallel to axis 526 of third pulley 516 as well as nonparallel to axes 422 and 524 of pulleys 512 and 514. The angled axis of rotation 526 allows guide pulley 518 to guide tension element 508 toward counterbalance spring 520, as described in greater detail below.

In some implementations, first pulley 512, second pulley 514, third pulley 516, and the curved surface of curved element 517 have the same diameter (e.g., same radius). Guide pulley 518 can also have the same diameter.

Counterbalance spring 520 can be located approximately below guide pulley 518 as shown in FIGS. 5 and 6. In some implementations, spring 520 can be located and oriented in a manner to allow it to fit within the housing of first link 412. For example, in the implementation of FIG. 4, first link 412 is curved, and spring 520 is angled to fit within the curved interior volume of first link 412.

A first end of spring 520 is mechanically grounded by being coupled to first link 412, e.g., to frame portion 531 that is coupled to link 412. A second end of spring 520 is coupled to tension member 508 and can provide a spring force on the tension member. In some examples, as shown, the first end of spring 520 can be the further end of the spring and the second end can be closer to guide pulley 518, such that the second end is moved away from the first end to provide tension via stretch of the spring. In other examples, the first end of spring 520 can be the end closer to guide pulley 518 and the second end of spring 520 is the further end at frame portion 531, such that the second end is moved toward the first end to compress the spring.

Tension element 508 has a first end coupled to spring 520. Tension element 508 is routed from its first end at spring 520 to guide pulley 518, where it wraps at least partially around guide pulley 518. From guide pulley 518, tension element 508 is routed to and at least partially wraps around third pulley 516. From pulley 516, tension element 508 is routed to and is wrapped at least partially around first pulley 512 and then is routed to and is wrapped at least partially around second pulley 514. Tension element 508 then is routed back toward third pulley 516, where it wraps at least partially around the curved surface of curved element 517. Tension element 508 is anchored at its second end (e.g., at an opposite end to the first end of tension element 508) to mechanical ground, e.g., coupled to grounded element 534 that can be coupled to frame portion member 530 and/or first link 412, or coupled to curved element 517 that is rigidly coupled to first link 412. In various implementations, tension element 508 can be wrapped around curved element 517 by a different amount depending on the implementation, e.g., depending on the range of motion of second link 414 and/or counterbalance arm 506.

Figure 7A:
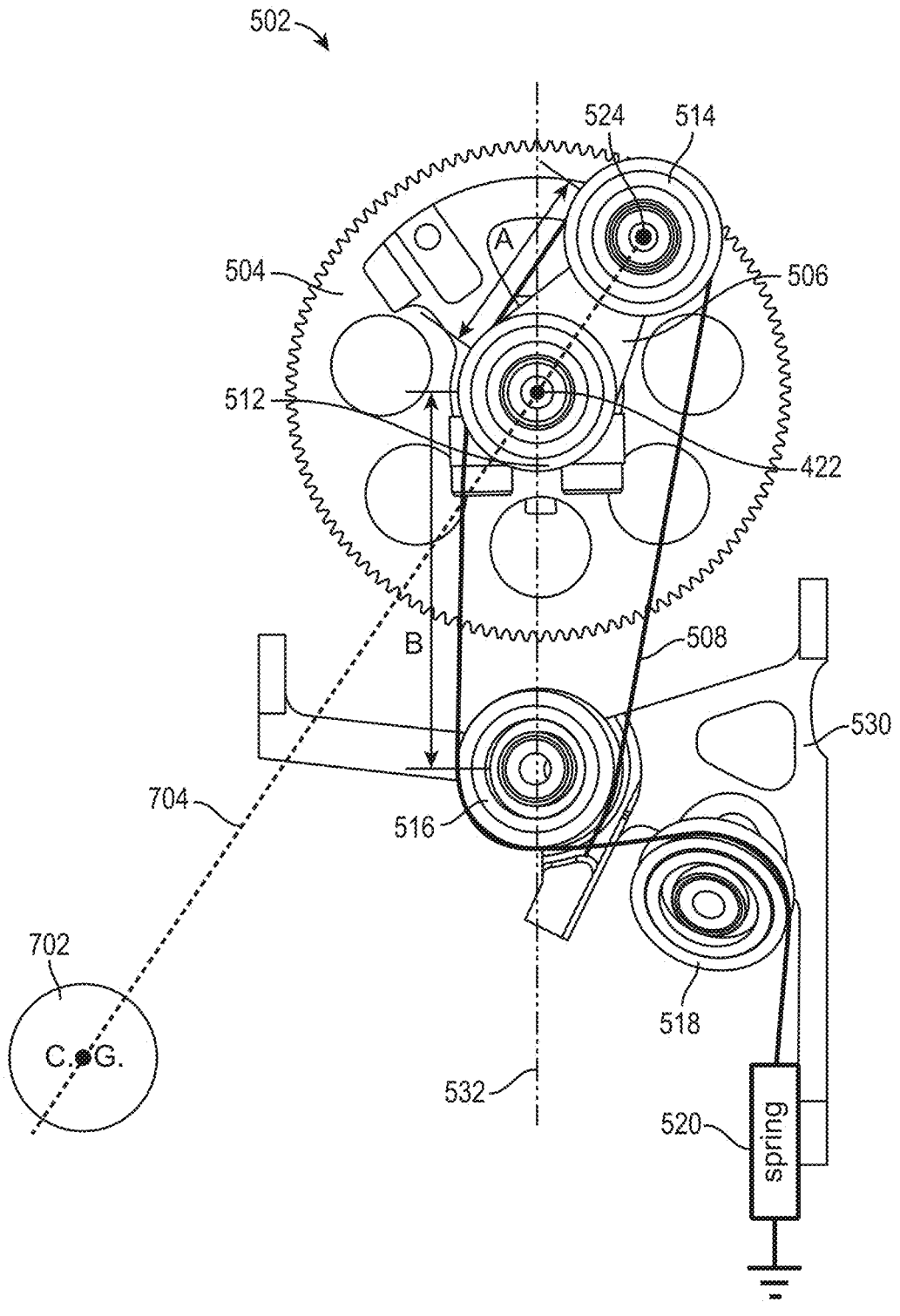
FIGS. 7A and 7B are front views of the counterbalance mechanism of FIG. 6 in first and second configurations, respectively, according to some implementations.

FIG. 7A is a front view of counterbalance mechanism 502 in a first configuration. In some implementations, this configuration can be operated by a particular hand of a user of a control input device and arm assembly that is coupled to counterbalance mechanism 502. In some examples, this configuration can be provided in control input arm assembly 400 of FIG. 4 as arm assembly 310 of FIG. 3 that is operated by a left hand of a user.

Configurable arm 506 is rotatable about axis 422 to different orientations, and this rotation can be used to configure the counterbalance mechanism 502 to loads having different spatial locations relative to the counterbalance mechanism. For example, in FIG. 7A, configurable arm 506 is oriented in a first configuration orientation, which in this view is an orientation that is clockwise (e.g., a right direction) from a vertical orientation aligned with a vertical axis 532 intersecting axis 422.

The first orientation shown in FIG. 7A is suited to counterbalancing a mass that has a center of gravity 702 located on the opposite side of axis 422 from the second pulley 514, e.g., on the left side of vertical axis 532 that intersects axis 422 in the view shown. For example, center of gravity 702 can be the center of gravity of the mass that is coupled to joint gear 504 and rotates about axis 422. That mass includes second link 414 and control input device 408 as shown in FIG. 4. The counterbalance mechanism 502 and center of gravity 702 can be one implementation of the counterbalance mechanism 100 shown in FIG. 1.

In this example, an axis 704 intersects center of gravity 702, axis of rotation 422 of first pulley 512, and axis of rotation 524 of second pulley 514. Configurable arm 506 has a length defined by a first portion and a second portion, such that first pulley 512 is coupled to the first portion at axis 422 and second pulley 514 is coupled to the second portion (e.g., at a second end of the configurable arm). The length of configurable arm 506 is aligned with axis 704 that intersects axis of rotation 524, axis of rotation 422, and the center of gravity 702 of the load of the counterbalance mechanism.

Counterbalance mechanism 502 includes first pulley 512 and second pulley 514 that are spaced apart by a distance A. First pulley 512 and third pulley 516 are spaced apart by a distance B. For example, these dimensions can be based on the dimensions a and b as described above with reference to FIG. 1 to provide a counterbalance force on the mass having center of gravity 702 to oppose the force of gravity on that mass.

Figure 7B:
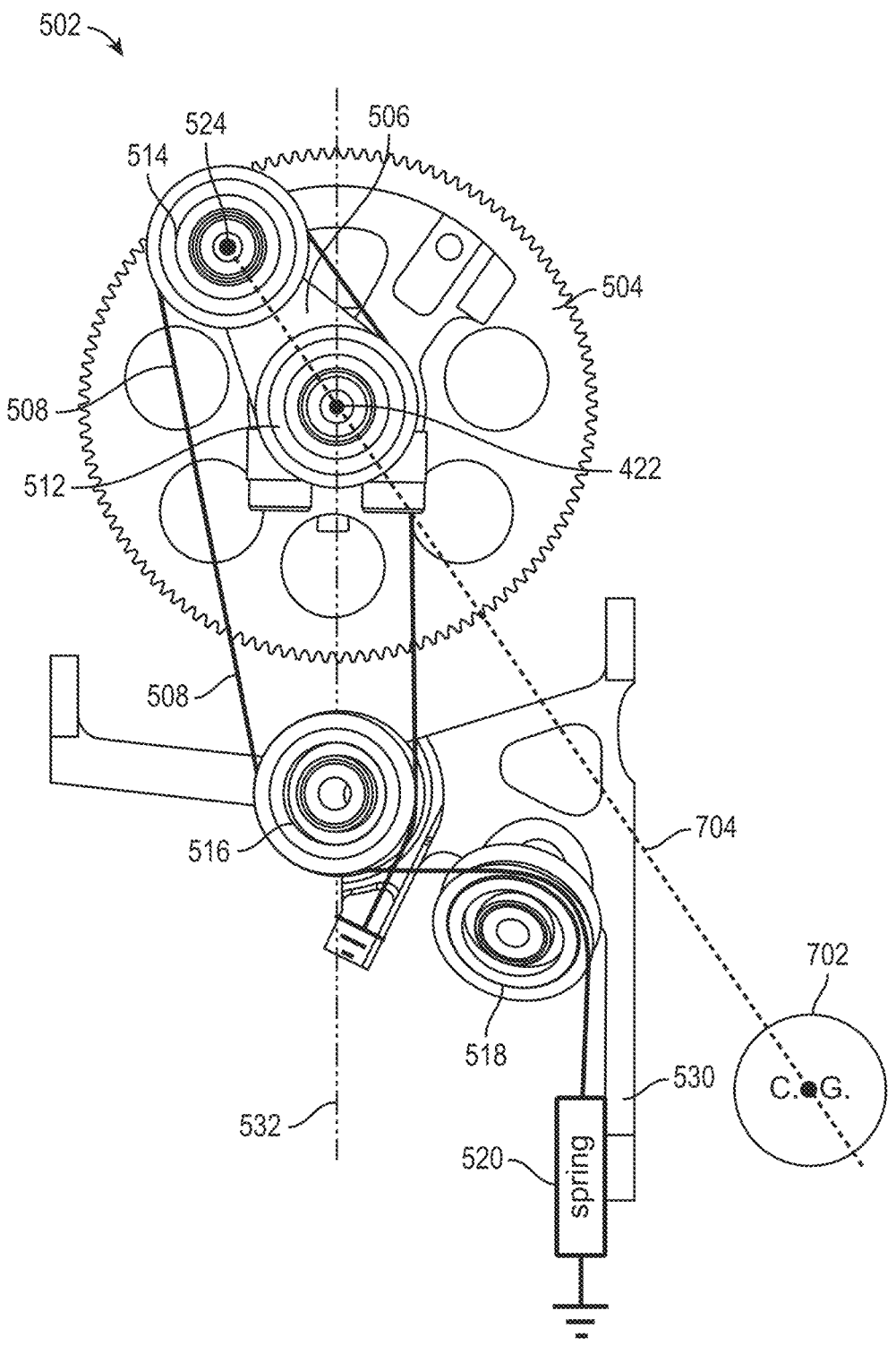
Figure 12:
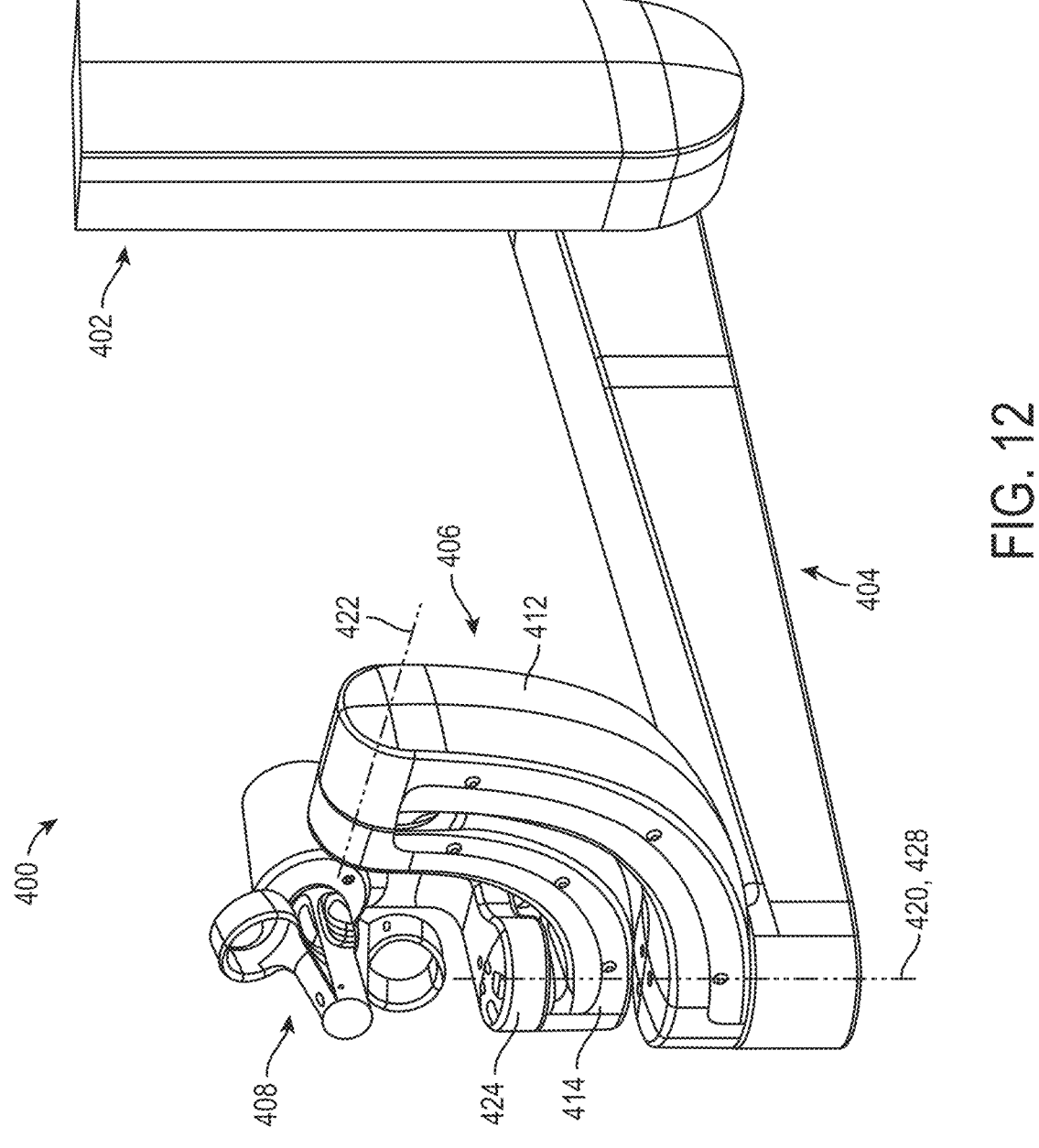
FIG. 12 is a perspective view of the portion of control input arm assembly of FIG. 4 in which the arm assembly has been reconfigured to a right-handed configuration, according to some implementations.

FIG. 7B is a front view of counterbalance mechanism 502 in a second configuration. In some implementations, this configuration can be used for operation by a different hand of the user of a control input device of and arm assembly than the hand used for the first configuration shown in FIG. 7A. In some examples, the second configuration in control input arm assembly 400 of FIG. 4 as arm assembly 312 of FIG. 3 that is operated by a right hand of a user, as also shown in FIG. 12.

In FIG. 7B, configurable arm 506 has been rotated counterclockwise with respect to the first orientation shown in FIG. 7A, to be oriented in a second configuration orientation, which in this view is counterclockwise or in a left direction from a vertical orientation aligned with a vertical axis intersecting axis 422.

Similarly to the first configuration of FIG. 7A, axis 704 intersects center of gravity 702, axis of rotation 422 of first pulley 512, and axis of rotation 524 of second pulley 514. The length of configurable arm 506 is aligned with axis 704.

The second orientation as shown in FIG. 7B is suited to counterbalancing a mass that has center of gravity 702 located on the opposite side of axis 422 from the second pulley 514, e.g., on the right side of vertical axis 532 that intersects axis 422 in the view shown. In this example, the counterbalance mechanism 502 is configured to counterbalance a center of gravity 702 that has been approximately mirrored across vertical axis 532 extending through axis 422 from the orientation of center of gravity 702 shown in the configuration of FIG. 7A. This is suitable for a right handed configuration of the control input device 408, as shown in FIG. 12.

Thus, counterbalance mechanism 502 can be configured for a left- or right-sided load center of gravity (e.g., on either side of vertical axis 532) by orbiting second pulley 514 about axis 422, via the rotation of configurable arm 506, to the opposite side of vertical axis 532 from the center of gravity. Before and after this orbiting, the center of the second pulley is intersected by axis 704 that intersects the center of gravity and axis 422. This configuration can be performed without having to move the axis of rotation of other components such as third pulley 516, and thus can accommodate centers of gravity that are located a far distance or angle from the vertical axis 532 without having to provide a larger housing for the counterbalance mechanism. Furthermore, the tension of cable 508, as well as the stretch of the counterbalance spring 520 when the load is in a home position, remain the same in any configuration of configurable arm 506, so that the same counterbalance force is consistently provided in the various configurations of the counterbalance mechanism.

Figure 8:
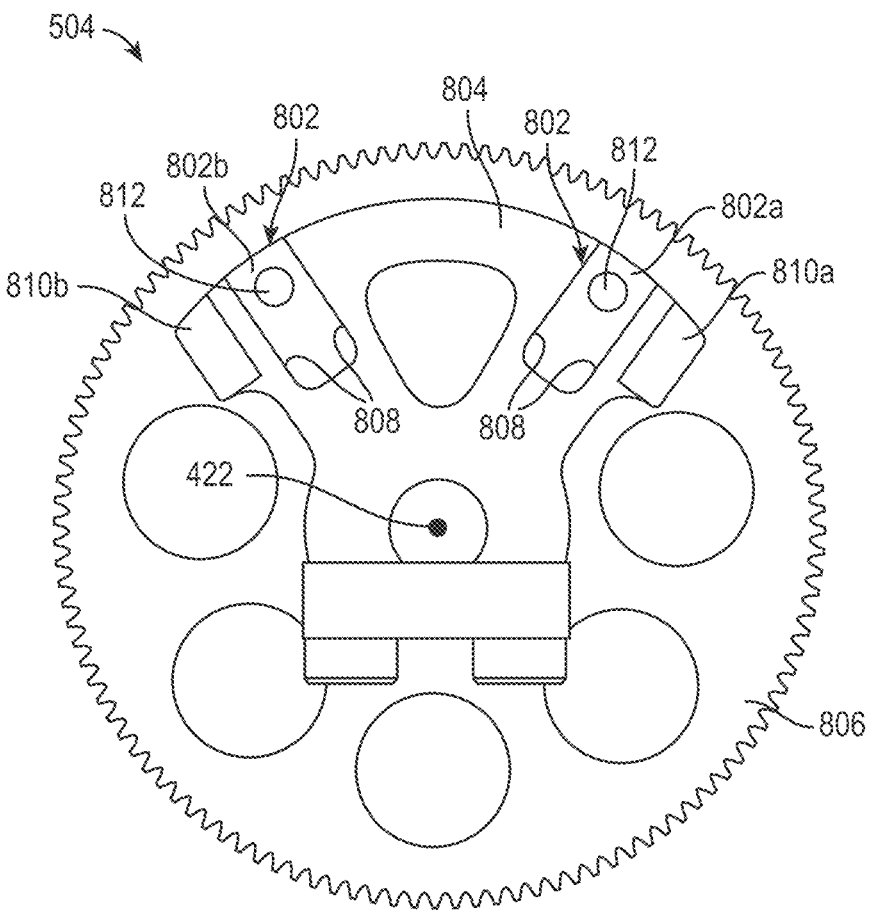
FIG. 8 is a front view of an example implementation of a joint gear of the counterbalance mechanism of FIGS. 5-7B, according to some implementations.

FIG. 8 is a front view of an example implementation of joint gear 504 of the counterbalance mechanism 502 described with reference to FIGS. 5-7B. Joint gear 504 is rigidly coupled to second link 414 and control input device 408 as described above. In some implementations, joint gear 504 includes gear teeth on its outer circumferential surface that engage other gear teeth of one or more gears coupled to an actuator, sensor, and/or mechanical element. Joint gear 504 can be a different base element in other implementations, as described above.

Joint gear 504 includes multiple engagement elements, where each engagement element is associated with a particular configuration orientation of configurable arm 506 about axis 422. In the example implementation of FIG. 8, each engagement element is a configuration slot 802. Two configuration slots 802a and 802b are included in joint gear 504 as shown in FIG. 8. Each configuration slot 802 guides and engages the configurable arm 506 at its associated configuration orientation. For example, configuration slot 802a engages the configurable arm 506 at the first configuration orientation described with reference to FIG. 7A. Configuration slot 802b engages configurable arm 506 at the second configuration orientation described with reference to FIG. 7B. In other implementations, different or additional engagement elements can be provided at different configuration orientations about axis 422. For example, an engagement element can be a plug element or extension that extends from the surface of joint gear 504, or other feature that can be engaged with and/or secured to configurable arm 506.

In some implementations, configuration slots 802a and 802b are recessed into a raised portion 804 of the joint gear 504. For example, portion 804 of joint gear 504 can be raised above or extend past a surface of base portion 806 of joint gear 504. For example, base portion 806 can include gear teeth in some implementations, as shown in FIG. 8. Slots 802 are approximately rectangular in the example of FIG. 8, but can have other shapes in other implementations (e.g., triangular, hexagonal, etc.).

In some implementations, slots 802 can have one or more tapered sides 808, e.g., sloped or beveled slides of each slot 802 that slope from the top of portion 804 toward a center of the slot 802. The tapered slides of a slot 802 can assist and guide the configurable arm 506 to slide into an orientation about axis 422 in which it can engage with the slot.

In the example implementation, each slot 802 includes an aperture 812, which can be used to secure configurable arm 506 to joint gear 502. For example, each aperture 812 can be a threaded aperture that can receive a bolt or screw, e.g., the bolt described with respect to FIG. 10.

Joint gear 504 includes multiple stop members 810, each of which can be used to assist and/or guide configurable arm 506 into the slot 802 associated with the stop member 810. For example, two stop members 810a and 810b are shown in FIG. 8. Each stop member 810 includes a protrusion raised above the surface of portion 804 of the joint gear 504 in the path of rotation of configurable arm 506 about axis 422.

Each stop member 810 provides a stop to the rotation of the configurable arm 506 about axis 422 in a particular direction, e.g., when rotating configurable arm 506 from one configuration orientation to another configuration orientation. The stop members 810 are located such that the configurable arm 506 can be engaged, at the stopped orientation, with the slot 802 located at that configuration orientation. For example, stop member 810a stops rotation of configurable arm 506 in a clockwise direction at an orientation that is aligned or approximately aligned to the first configuration orientation described with reference to FIG. 7A, and the configurable arm 506 can then be engaged with slot 802a (e.g., guided by a guide member of arm 506 as described below) to obtain the first configuration orientation. Stop member 810b stops rotation of configurable arm 506 in a counterclockwise direction at an orientation that is aligned or approximately aligned to the second configuration orientation described with reference to FIG. 7B, and the configurable arm 506 can then be engaged with slot 802b (e.g., guided by the guide member of arm 506) to obtain the second configuration orientation. In other implementations, different types of stop members can be provided at different configuration orientations about axis 422.

FIGS. 9A, 9B, and 9C are front, side cross-sectional, and perspective views, respectively, of an example configurable arm 506 that can be used in one or more implementations described herein. Configurable arm 506 can include an extended portion 902 that can act as a hub to which the second pulley 514 is rotatably coupled. For example, second pulley 514 can include a pulley portion 904 and a bearing 906, where bearing 906 is rigidly coupled to extended portion 902 and pulley portion 904 is rotatably coupled to bearing 906. Bearing 906 can be a ball bearing or other rotatable bearing that allows pulley portion 904 to rotate about axis 522 with respect to extended portion 902 and configurable arm 506.

In some implementations, first pulley 512 can be rotatably coupled to shaft 522. For example, first pulley 512 can include a pulley portion 908 and a bearing 910, where bearing 910 is rigidly coupled to shaft 522 and pulley portion 908 is rotatably coupled to bearing 910. Bearing 910 can be a ball bearing or other rotatable bearing that allows pulley portion 908 to rotate about axis 422 with respect to shaft 522 and configurable arm 506.

Configurable arm 506 includes a shaft aperture 912 that can receive a shaft and a bolt aperture 914 that can receive a bolt or similar attachment member. In an example implementation (e.g. as shown in FIGS. 5-8), configurable arm 506 can be rotatably coupled to shaft 522 that extends through shaft aperture 912 such that configurable arm 506 can rotate about axis 422 as shown in FIGS. 7A and 7B.

An attachment mechanism can be used to secure configurable arm 506 to joint gear 504. In some implementations, the attachment mechanism can include an attachment member such as bolt 915 (shown in dotted lines in FIG. 9B) and threaded apertures 812 of joint gear 504, where bolt 915 is inserted through bolt aperture 914 and into one of the threaded apertures 812 of joint gear 504 to secure configurable arm 506 in a particular configuration orientation. One example of such a bolt is bolt 1000 described with respect to FIG. 10.

In some implementations, bolt aperture 914 can include a threaded portion 916 and a clearance portion 918, where threaded portion 918 is closer than threaded portion 916 to the surface 922 of configurable arm 506 that faces joint gear 504. When inserting bolt 915, a threaded portion of the bolt can be threaded through threaded portion 916, moved through clearance portion 918, and threaded into a threaded aperture 812 of joint gear 504. When removing the bolt to allow configurable arm 506 to be rotated to a different configuration orientation, the threaded portion of the bolt can be unthreaded and moved away from the threaded aperture 812 so that the threaded portion of the bolt is positioned at least partially within clearance portion 918 of bolt aperture 914.

In some implementations, configurable arm 506 can include a guide portion that engages the engagement element (e.g., slot 802) at each configuration orientation of joint gear 504. In the example implementation, the guide portion of arm 506 is a plug portion 920 that can engage any of slots 802 of joint gear 504. In other implementations, the guide portion can be a different engagement element, e.g., a slot in configurable arm 506 that can be engaged by a plug element of joint gear 504 or coupled to joint gear 504, or other feature that can be secured to each engagement element of joint gear 504.

Plug portion 920 is an extended portion of arm 506 that is located on the side of configurable arm 506 facing joint gear 504 and opposite the threaded portion 916 of bolt aperture 914. Plug portion 920 can surround clearance portion 918 of bolt aperture 914. Plug portion 920 is sized and shaped to be inserted into any of the slots 802 of joint gear 504 to engage configurable arm 506 with joint gear 504 at one of the configuration orientations. For example, plug portion 920 fits within a slot 802 such that an engaging surface of plug portion 920 contacts the flat bottom surface of the slot 802 and a surface 922 of configurable arm 506 contacts portion 804 of the joint gear 504. In some implementations, plug portion 920 is a tapered element including multiple tapered sides 924 that assist and guide the configurable arm 506 into a slot 802. In some implementations, tapered sides 924 contact and engage tapered sides 808 of slot 802.

In some implementations, configurable arm 506 can include one or more slots 930 to assist a user in separating configurable arm 506 from joint gear 504. For example, each slot 930 can be configured to receive a separation tool to move (e.g., slide or pry) the configurable arm away from the base element. In some examples, the user can insert the separation tool that has a portion that fits within a slot 930 to be positioned between the configurable arm 506 and joint gear 504, such that the user can pull on an extended portion of the separation tool (extending out of slot 930) to contact and force the tool against the joint gear 504 and slide or pry the configurable arm 506 along shaft 522 and away from joint gear 504. Slots 930 can be located on configurable arm 506 close to shaft aperture 912 (e.g., located on an edge of the first portion or first end of configurable arm 506, that is between the shaft aperture 912 and bolt aperture 914). This location reduces the tendency of arm 506 to tilt and bind on shaft 522 when arm 506 is pulled along the shaft, which may happen more readily if configurable arm 506 is pulled at locations further away from shaft 522. In some implementations, slots 930 are shaped and configured to receive an end of a particular user-manipulated tool (e.g., wrench, etc.) that can also fit into the head of bolt 915 (or bolt 1000) and allow the user to screw or unscrew the bolt.

Different forms of configuration arm 506 can be used in other implementations, e.g., having a different shape, engagement elements, and/or attachment mechanism to secure the configuration arm in a configuration orientation for use in counterbalance mechanism 502. For example, the engagement element and/or attachment mechanism can include an aperture or slot in configuration arm 506 that can engage a pin, screw, or other engagement element of joint gear 504.

Figure 10:
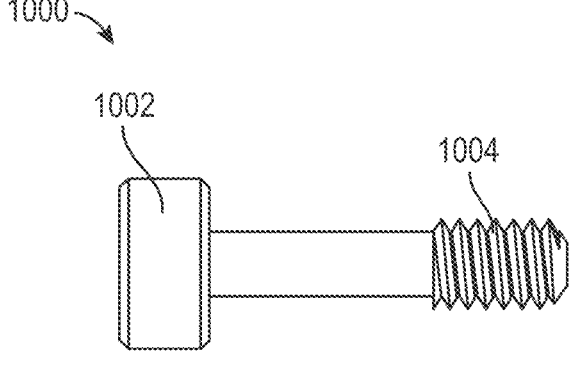
FIG. 10 is a side elevational view of an example bolt that can be used to secure the configuration arm to the joint gear in the counterbalance mechanism of FIGS. 5-7B, according to some implementations.

FIG. 10 is a side elevational view of an example bolt 1000 that can be used to secure configuration arm 506 to joint gear 504. Bolt 1000 includes a head portion 1002 and a threaded portion 1004. Bolt 1000 can be inserted in bolt aperture 914 shown in FIG. 9 and screwed into one of the threaded apertures 812 of the joint gear 504 to secure the configuration arm 506 to a particular configuration orientation about axis 422. Head portion 1002 engages a surface of configuration arm 506 that is opposite to surface 922 when the bolt 1000 is fully inserted in bolt aperture 914. In other implementations, other types of attachment elements instead of bolt 1000 can be used in an attachment mechanism to secure configurable arm 506 to joint gear 504.

FIGS. 11A-11D are perspective views of a portion 1100 of counterbalance mechanism 502 including joint gear 504 and configurable arm 506 in which arm 506 is in different orientations and positions, according to some implementations. These views show an example of configurable arm 506 being changed from one configuration orientation to a different configuration orientation.

Figures 11A, 11B:
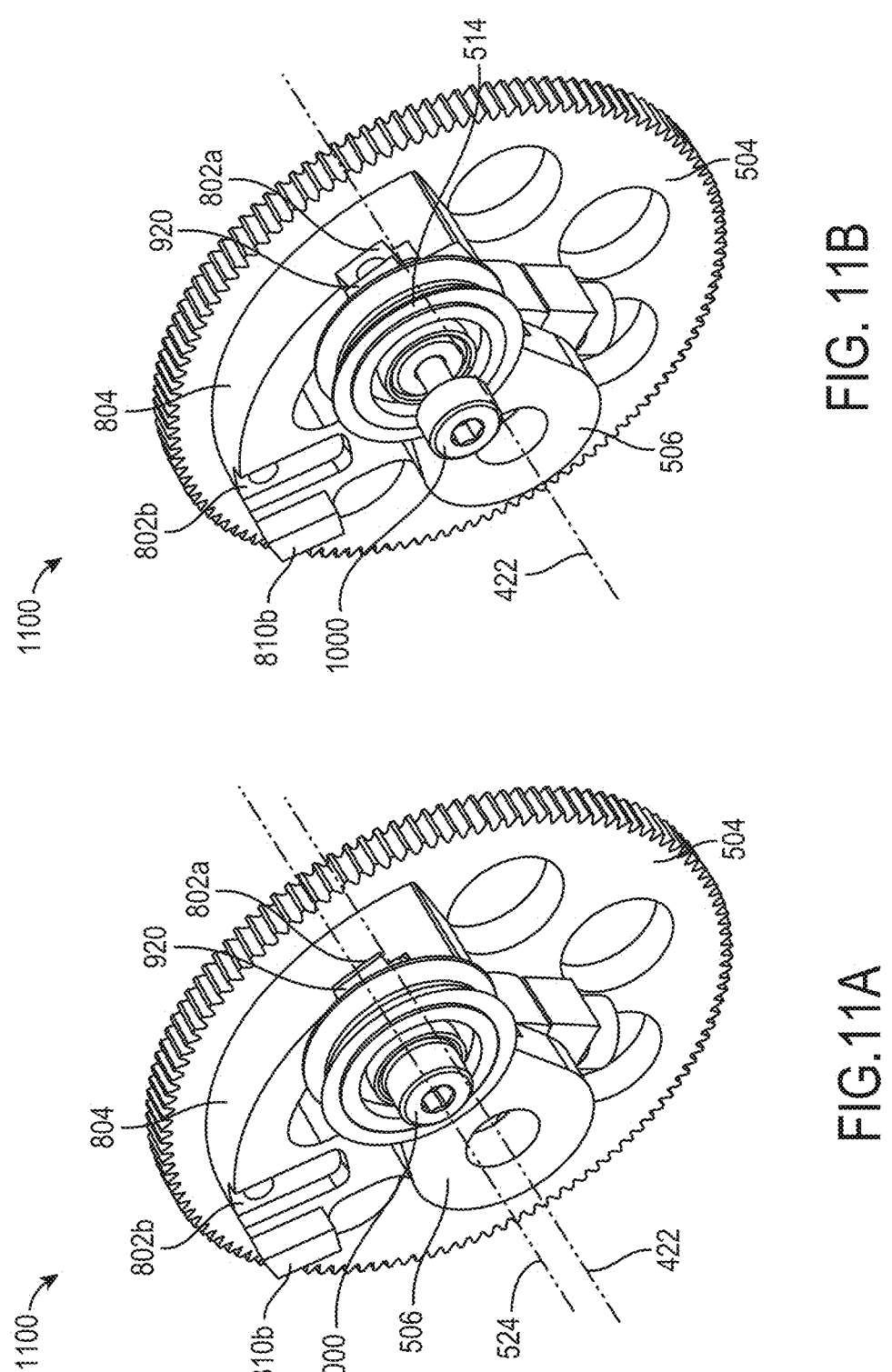
FIGS. 11A, 11B, 11C, and 11D are perspective views of a portion of the counterbalance mechanism of FIGS. 5-7B in which a configurable arm is in different orientations and positions, according to some implementations.

In FIG. 11A, configurable arm 506 is oriented at the first configuration orientation as described with reference to FIG. 7A. In this example, arm 506 is fully engaged with joint gear 504 by bolt 1000 that secures arm 506 to the joint gear 504, e.g., the plug portion 920 of configurable arm 506 is engaged with (seated in) slot 802a of joint gear 504 and bolt 1000 is screwed into threaded aperture 812 in slot 802a. As described above, in some implementations this first configuration orientation can be used for a left-handed configuration of control input arm assembly 400 of FIG. 4.

In FIG. 11B, configurable arm 506 has been pulled from slot 802a of joint gear 504 with respect to its secured position shown in FIG. 11A, to a disengaged position. Arm 506 has been pulled along axis 422 away from joint gear 504, e.g., along shaft 522 that couples the counterbalance mechanism 502 to second link 414. In some examples, arm 506 is moved along a shaft in a direction along axis 422 and perpendicular to a plane of rotation of the configurable arm. To obtain this position of arm 506, bolt 1000 is unscrewed from threaded aperture 812 in slot 802a and the bolt is pulled away from slot 802a (e.g., along axis 524) such that it is retracted at least partially into clearance portion 918 of configurable arm 506 sufficiently such that the bolt clears the sides of slot 802a. Configurable arm 506 is pulled away from slot 802a on shaft 522 sufficiently such that the engaging side of configurable arm 506 clears the sides of the slot 802a and the arm 506 can be rotated about axis 422. For example, in some implementations, the user can insert a tool into a slot 930 (or two tools into both slots 930) of configurable arm 506 to assist the user in pulling configurable arm 506 away from slot 802a.

Figures 11C, 11D:
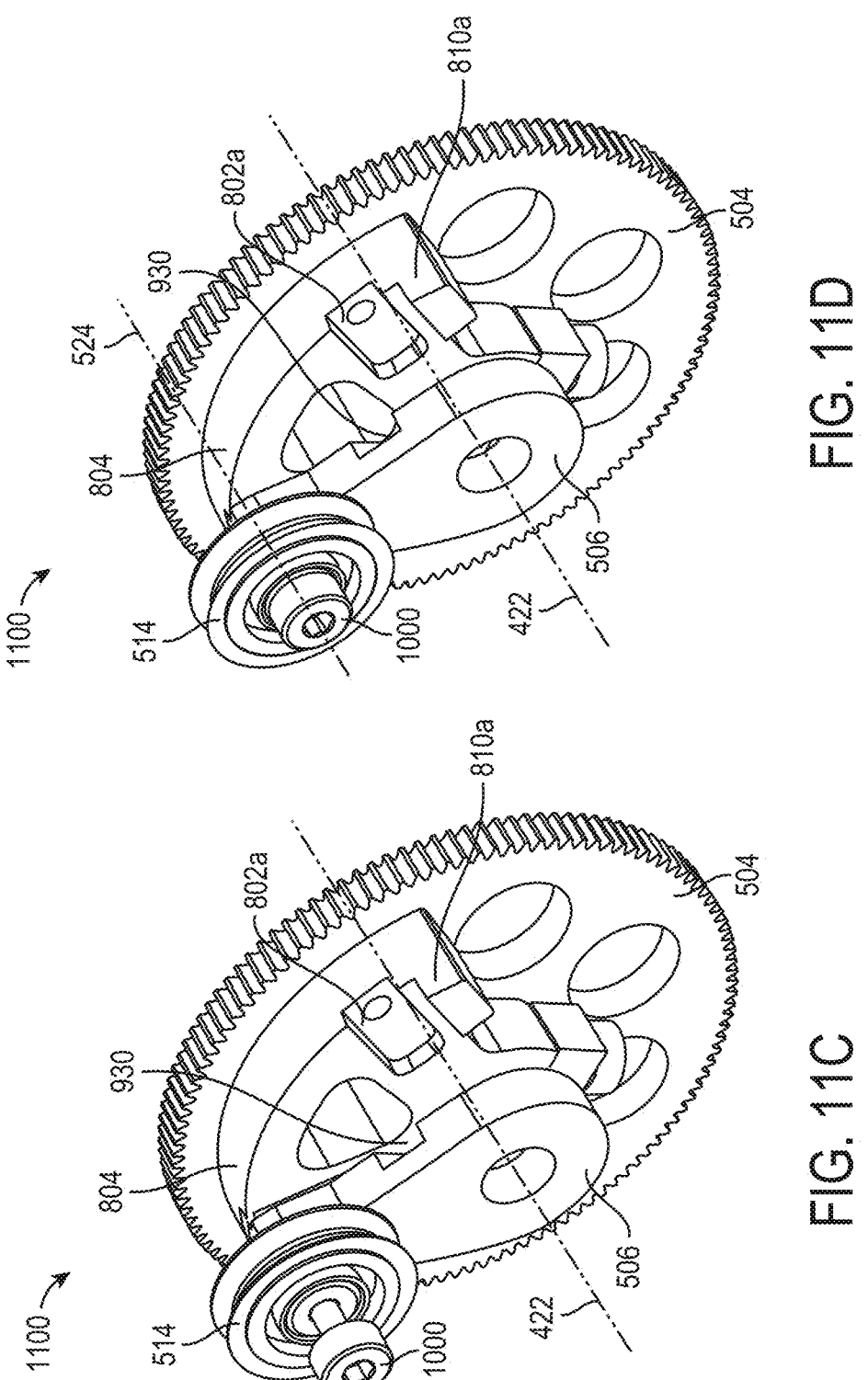

In FIG. 11C, configurable arm 506 has been rotated from its orientation shown in FIG. 11B. For example, arm 506 is rotated counterclockwise about axis 422 to obtain the orientation shown in FIG. 11C that is aligned or approximately aligned with the second configuration orientation designated by slot 802a of joint gear 504. In some implementations, the user can rotate configurable arm 506 counterclockwise until arm 506 is stopped by stop member 810b at an orientation that is aligned or approximately aligned with the second configuration orientation.

In FIG. 11D, configurable arm 506 has been moved with reference to FIG. 11C to a secured position at the second configuration orientation as described with reference to FIG. 7B. In this example, arm 506 is fully engaged with joint gear 504 by bolt 1000 that secures arm 506 to the joint gear 504, e.g., the plug portion 920 of configurable arm 506 is engaged with slot 802b of joint gear 504 and bolt 1000 is screwed into threaded aperture 812 in slot 802b along axis 514. As described above, in some implementations this first configuration orientation can be used for a right-handed configuration of control input arm assembly 400 of FIG. 4.

To obtain the second configuration orientation and secured position of arm 506, a user can push the configurable arm 506 along shaft 522 from its position of FIG. 11C into slot 802b of joint gear 504. The tapered sides 924 of plug portion 920 of configurable arm 506 can contact tapered sides 808 of slot 802b such that these tapered sides 924 and 808 guide plug portion 920 into slot 802b, thus precisely guiding configurable arm 506 to the second configuration orientation (relative to the more approximate alignment to the second configuration orientation obtained by moving configurable arm 506 against stop member 810b shown in FIG. 11C). After full insertion into slot 802b such that plug portion 920 is seated in (engaged with) slot 820b, the user can screw bolt 1000 into threaded aperture 812 in slot 802b such that the configurable arm 506 is secured in slot 802b.

A similar procedure in reverse of the process shown in FIGS. 11A to 11D can be performed, e.g., to change the configurable arm 506 from the second configuration orientation to the first configuration orientation, including moving the arm 506 in a clockwise direction about axis 422.

In various implementations, other or additional configuration orientations can be provided in a counterbalance mechanism. For example, a configuration orientation can be provided that counterbalances a mass having a center of gravity that is slightly different than center of gravity 702, e.g., has a different orientation about axis 422 than the center of gravity 702 shown in FIG. 7A but not as large a difference in orientation as the center of gravity 702 of FIG. 7B at the opposite side of the counterbalance mechanism. For example, a different control input device, or component thereof, could be used in control input arm assembly 400 in place of the control input device 408 or component that provides the center of gravity 702 of FIG. 7A. In some examples of these implementations, a third configuration orientation can be provided clockwise or counterclockwise about axis 422 from the first configuration orientation, and can have its own associated slot 802, threaded aperture 812, and (removable) stop member 810 (e.g., replacing or provided in addition to the second configuration orientation slot 802). In some examples, the configurable arm 506 can be moved to the third configuration orientation if the associated component is attached to the control input arm assembly 400.

In some implementations, configuration of counterbalance mechanism 502 can also be performed by adjusting other components of the counterbalance mechanism. For example, the distance A between first pulley 512 and second pulley 514 (shown in FIG. 7A) can be adjusted, e.g., by moving second pulley 514 along axis 704 and along configurable arm 506. For example, such an adjustment of a pulley can counterbalance a different load that is heavier or lighter than the load having center of gravity 702, e.g., a different load that has the same orientation of center of gravity 702 about axis 422 (a tension element 508 of different length may be used in some implementations). In some implementations, third pulley 516 can be moved. For example, third pulley 516 can be slidably coupled ground member 530, e.g., slidable within a groove or channel of the ground member. The third pulley 516 can be slid to either end of the channel to configure counterbalance mechanism 502 to counterbalance masses having centers of gravity at different orientations about axis 422.

In some implementations, a doubled tension element (e.g., doubled cable) can be used in some implementations of counterbalance mechanisms that include one or more features described herein. For example, a doubled tension element can be used in place of the single tension element 508 shown in FIGS. 5-8. In some examples, two cables routed side-by-side can have one end coupled to spring 520 and their other ends coupled to ground at grounded element 534.

FIG. 12 is a perspective view of the portion of control input arm assembly 400 of FIG. 4 in which arm assembly 400 has been reconfigured from its left-handed configuration to a right-handed configuration, according to some implementations. In some examples as shown in FIGS. 4-11D, configurable arm 506 of counterbalance mechanism 502 in first link 412 has been moved from the first configuration orientation at slot 802a of joint gear 504 to the second configuration orientation at slot 802b of joint gear 504, as shown in FIGS. 11A-11D.

After this reconfiguration of configurable arm 506, housing of arm assembly 400 can be replaced and the links of arm assembly 400 can be rotated to obtain the right-handed configuration. For example, a user can rotate the links manually or actuators in one or more links can be controlled by a control system to move the links. As shown in FIG. 12, in the right-handed configuration, first link 412 has been rotated 180 degrees from its position shown in FIG. 4, which causes second link 414 to also be rotated 180 degrees since it is supported by first link 412. Control input device 408 is rotated 180 degrees about axis 428 with reference to first link 412 and second link 414 (e.g., is not rotated with respect to members 402 and 404 of arm assembly 400), to maintain an orientation that is similar to its orientation in the left-handed configuration shown in FIG. 4 with reference to first member 402 and second member 404. Control input device 408 is thus oriented to be used by a right hand of the user, with first link 412 and second link 414 on the outside (e.g., to the right) of the user's hand.

Figure 13:
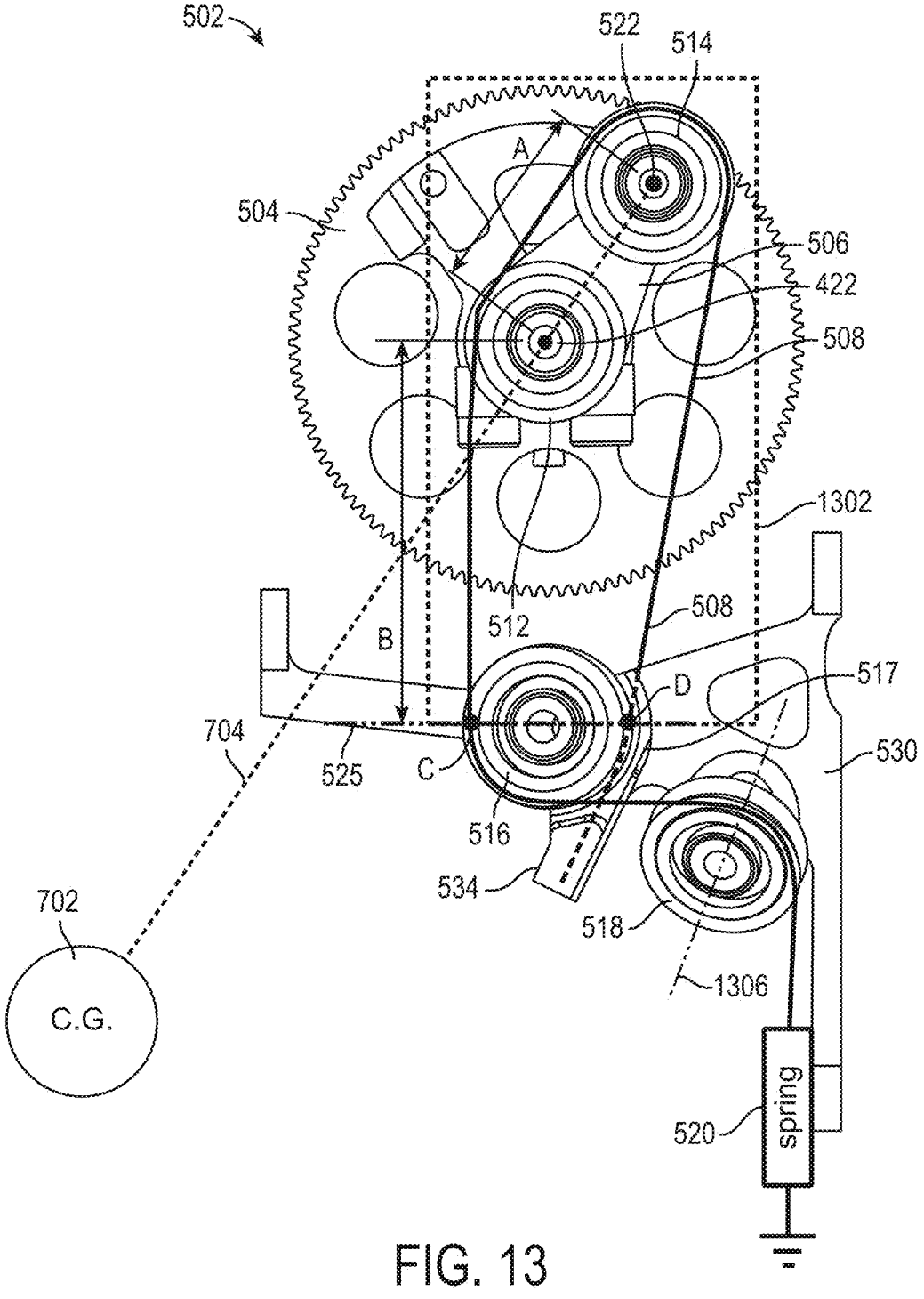
FIG. 13 is a front view of an example counterbalance mechanism showing planar counterbalance features, according to some implementations.
Figure 14:
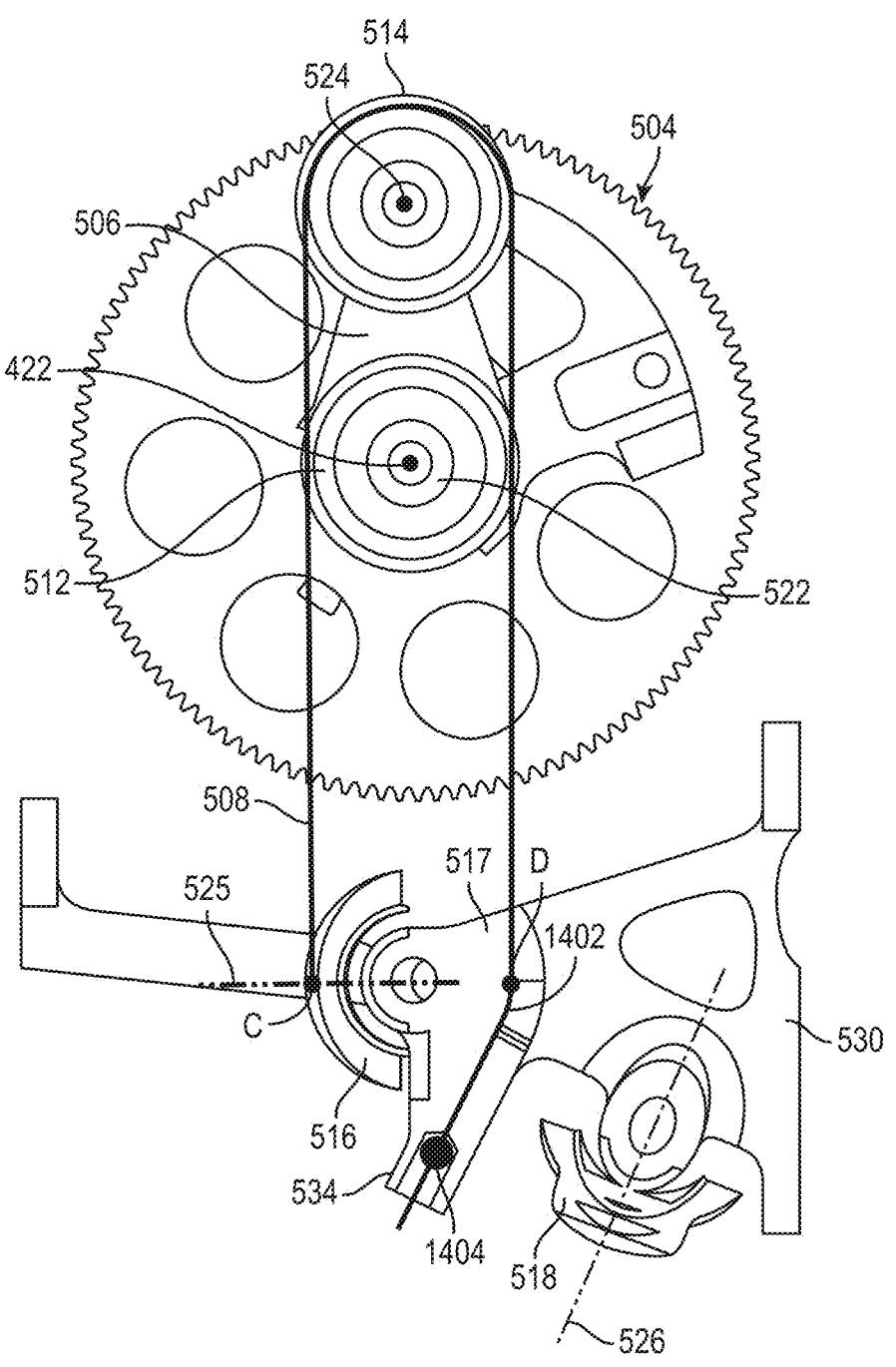
FIG. 14 is a side elevational view of the tension element, third counterbalance pulley, and curved element of the counterbalance mechanism of FIG. 13, according to some implementations.

FIG. 13 is a front view of an example of counterbalance mechanism 502 showing planar counterbalance features, according to some implementations. FIG. 14 is a cross section of some components of counterbalance mechanism 52 as cut by an active plane of counterbalance mechanism 502. These figures show some implementations of a counterbalance mechanism, which can be mechanism 502 and other counterbalance mechanisms, that include one or more features that provide active counterbalance components in a single plane. Such features allow, for example, more accurate counterbalance forces to be applied to a load.

In the implementation of FIGS. 13-14, first and second pulleys 512 and 514 have axes of rotation 422 and 524 that are parallel. Third pulley 516 has an axis of rotation 525 that is nonparallel to the axes of rotation 422 and 524 of the first and second pulleys 512 and 514. Third pulley 516 has been angled or tilted such that tension element 508 makes contact with third pulley 516 and curved element 517 in a single plane 1302 that also includes the first and second pulleys 512 and 514. Thus, plane 1302 is orthogonal to first pulley axis 422 and second pulley axis 524, and axis of rotation 525 of third pulley 516 is at a non-orthogonal angle with reference to plane 1302.

For example, in a path of tension element 508 from its first end at counterbalance spring 520 to its second end at grounded element 534, tension element 508 wraps around third pulley 516 and exits the third pulley 516 at a point C. After wrapping around first and second pulleys 512 and 514, tension element 508 enters contact with curved element 517 at point D and wraps around a curved surface 1402 of element 517 before being coupled to grounded element 534 (FIG. 14 shows third pulley 516, curved element 517, and guide pulley 518 partially due to the cross-sectional view based on plane 1302). In the example shown in FIG. 14, tension element 508 is anchored to grounded element 534 by a ball clip 1404; other attachment mechanisms can be used in other implementations.

To cause these planar exit and entrance of the tension element 508, third pulley 516 is angled such that a side of pulley 516 closer to point C is positioned within plane 1304 (and thus appears in FIG. 14) and a side of pulley 516 closer to point D is higher, e.g., further from and out of plane 1302 (and thus does not appear in FIG. 14). The out-of-plane side of third pulley 516 is further from the surface of frame portion 530 and thus allows curved element 517 to be located at a higher position, further from frame portion 530 and within plane 1304, than if axis 525 of pulley 516 were parallel to the other pulley axes 422 and 524.

The moment applied by a counterbalance mechanism 502 (and the mechanism as shown in FIG. 1) is $M_{cb}=K*A*B*\text{Sin}(\theta)$, which perfectly counteracts the moment load caused by gravity only if several conditions are met. These conditions include the spring rate, the initial tension of the system, and the active length of the tension element 508 are all in a single plane as indicated by plane 1302. Angling third pulley 516 as shown provides this active length of tension element 508 in a single plane. The other portions of tension element 508 (e.g., the length wrapping around the lower half of third pulley 516, the length wrapping around guide pulley 518, and the length extending to spring 520) are not considered in the counterbalance force determination, and so these portions need not be in the single plane 1302.

The curved surface 1402 of curved element 517 can be angled at the same angle as the circumferential sides of third pulley 516 that engage tension element 508. For example, a center orthogonal axis located at a radius of curved surface 1402 of curved element 517 can have the same angle as axis of rotation 525 of third pulley 516. For example, if curved element 517 is implemented as a cylinder (stationary pulley), the central axis of the cylinder is oriented in parallel to (and/or aligned with) the rotation axis 525 of third pulley 516.

The angle of third pulley 516 causes the active portions of the tension element 508 to be within plane 1304, the active portions being the portions of tension element 508 between first pulley 512, second pulley 514, and the points C and D as shown. This allows the moment load of the counterbalance and the moment load from gravity to cancel out for all possible angles. Since the determination of counterbalance forces from counterbalance mechanisms often assumes, ideally, that these active portions are in a single plane, the angle of third counterbalance pulley 516 provides counterbalancing performance that is closer to the ideal design, e.g., such that an appropriate sinusoidal force is produced to counterbalance gravity forces at any rotational angle of the load about axis 422. This planar feature allows a counterbalance mechanism to provide counterbalance forces that more accurately reduce or cancel gravity force on a load.

In some previous implementations, active portions of a tension element (including entry and exit) were not in a single plane because a stationary curved element was at a different level than the third pulley (e.g., adjacent to the third pulley) and the third pulley was not angled. Thus, the path of the tension element traced into three different planes, e.g., from one level of the curved element, to a level of the first and second pulleys 512 and 514, to a level of the third pulley 516. This caused the counterbalance mechanism to produce inappropriate counterbalance forces at some load angles where the counterbalance force did not fully cancel the gravity force on the load at all rotational orientations of the load. The model of the counterbalance mechanism assumed there was no offset or change in level of the different pulleys and elements.

Counterbalance mechanism 502 can also, in some implementations, provide the axis of rotation 526 of guide pulley 518 at an angle such that axis 526 is nonparallel to the rotation axes 422, 524, and/or 525 of their respective pulleys. The angle of guide pulley 518 can be arranged to route tension element 508 toward spring 520. Spring 520, for example, may be positioned and/or oriented at an angle offset from pulley rotation axes so that spring 520 can fit in available space of a housing of the arm assembly 400.

The angle of guide pulley 518 can be arranged to reduce or eliminate any fleet angle of tension member 508 that may exist going into or out of third pulley 516. The fleet angle is the angle at which a tension member such as a cable engages with (e.g., enters or exits) a pulley, as referenced from the center axis of the pulley. Guide pulley 518 can be angled such that tension member 508 engages the third pulley 516 and the guide pulley 518 at zero (or close to zero) angle offset from the center of the engaging circumferential surface or side of these pulleys. Such reduced fleet angle can reduce or eliminate friction provided from the engagement between tension member 508 and pulleys 516 and 518. The planar positioning of the entry and exit points C and D for third pulley 516 can also reduce the fleet angle of tension member 508 engaging with third pulley 516 and/or with curved element 517.

FIG. 15 is a flow diagram illustrating an example method 1500 to configure a counterbalance mechanism, according to some implementations. Method 1500 can, for example, be performed using counterbalance mechanism 502, any of the example counterbalance mechanisms described herein, or other counterbalance mechanisms. In some implementations, the counterbalance mechanism is coupled to or included in a mechanical arm assembly, such as arm assembly 400 as shown in FIG. 4 that can be included in a user control system 202 of FIG. 2. Other implementations can use a counterbalance mechanism provided in other types of mechanical systems, e.g., non-teleoperated systems.

In block 1502, a configurable arm of a counterbalance mechanism is oriented at a first configuration orientation and engaged with a base element. For example, as described in examples herein, configurable arm 506 of counterbalance mechanism 502 can be oriented in a first configuration orientation in which arm 506 is engaged with and secured to a base element that is joint gear 504. As shown in some examples herein, the first configuration orientation can be associated with a particular handedness of a control input device. For example, as shown in FIGS. 4 and 12, the first configuration orientation can be used with left-handed configuration of an arm assembly for use with a user's left hand. The method continues to block 1504.

In block 1504, an attachment mechanism that secures the configurable arm to the base element is disengaged. In some examples described above, the attachment mechanism includes a bolt 1000 that is unscrewed from threaded aperture 812 in slot 802a of joint gear 504. The method continues to block 1506.

In block 1506, the configurable arm is moved away from the base element along a shaft. In some implementations, a guide portion of the configurable arm disengages an engagement element of the base element. In some examples, plug portion 920 of configurable arm 506 disengages from a slot 802 of joint gear 504 and configurable arm 506 is slid along shaft 522 to a disengaged position along shaft 522, e.g., as shown in FIG. 11B. In some examples, a user can insert a tool in a slot 930 to assist sliding the configurable arm along the shaft without binding. For example, the configurable arm can be moved along the shaft in a direction \ perpendicular to a plane of rotation of the configurable arm. The method continues to block 1508.

In block 1508, the configurable arm is rotated toward target configuration orientation and against a stop member in the range of motion about an axis of rotation of the arm. In some implementations, as described above, the stop member is located such that the configurable arm is stopped at an orientation that is aligned or approximately aligned with the second configuration orientation of the base element. For example, if in block 1506 the configurable arm was moved out of the first configuration orientation of FIG. 11A, the configurable arm is rotated counterclockwise to a stopped orientation against stop member 910b, as shown in FIG. 11C. If in block 1506 the configurable arm was moved out of the second configuration orientation of FIG. 11D, the configurable arm is rotated clockwise (e.g., by a user) to a stopped orientation against stop member 910a, as shown in FIG. 11B. The stop member aligns the configurable arm and also provides a safety stop to the arm to prevent it from rotating past the target configuration orientation. The method continues to block 1510.

In block 1510, the configurable arm is moved toward the base element to engage the base element at the target configuration orientation. For example, configurable arm can be pushed by a user along shaft 522 toward joint gear 504 such that plug portion 920 of the configurable arm inserts into slot 802b at the second configuration position, as shown in FIG. 11D. The method continues to block 1512.

In block 1512, the attachment mechanism is engaged to secure the configurable arm to the base element at the second configuration position. In some examples, the attachment mechanism includes bolt 1000 that is screwed into threaded aperture 812 in slot 802b of joint gear 504. In some examples as described for FIGS. 4 and 12, the control device can then be operated in a right-handed configuration with the counterbalance mechanism 502 correctly balancing the gravity forces on the control input device 408 and second link 414.

It should be noted that the blocks described in the methods disclosed herein can be performed in a different order than shown and/or simultaneously (partially or completely) with other blocks, where appropriate. Further, not all of the described blocks need be performed in various implementations. In some implementations, blocks can be performed multiple times, in different orders, and/or at different times in the methods.

Figure 16:
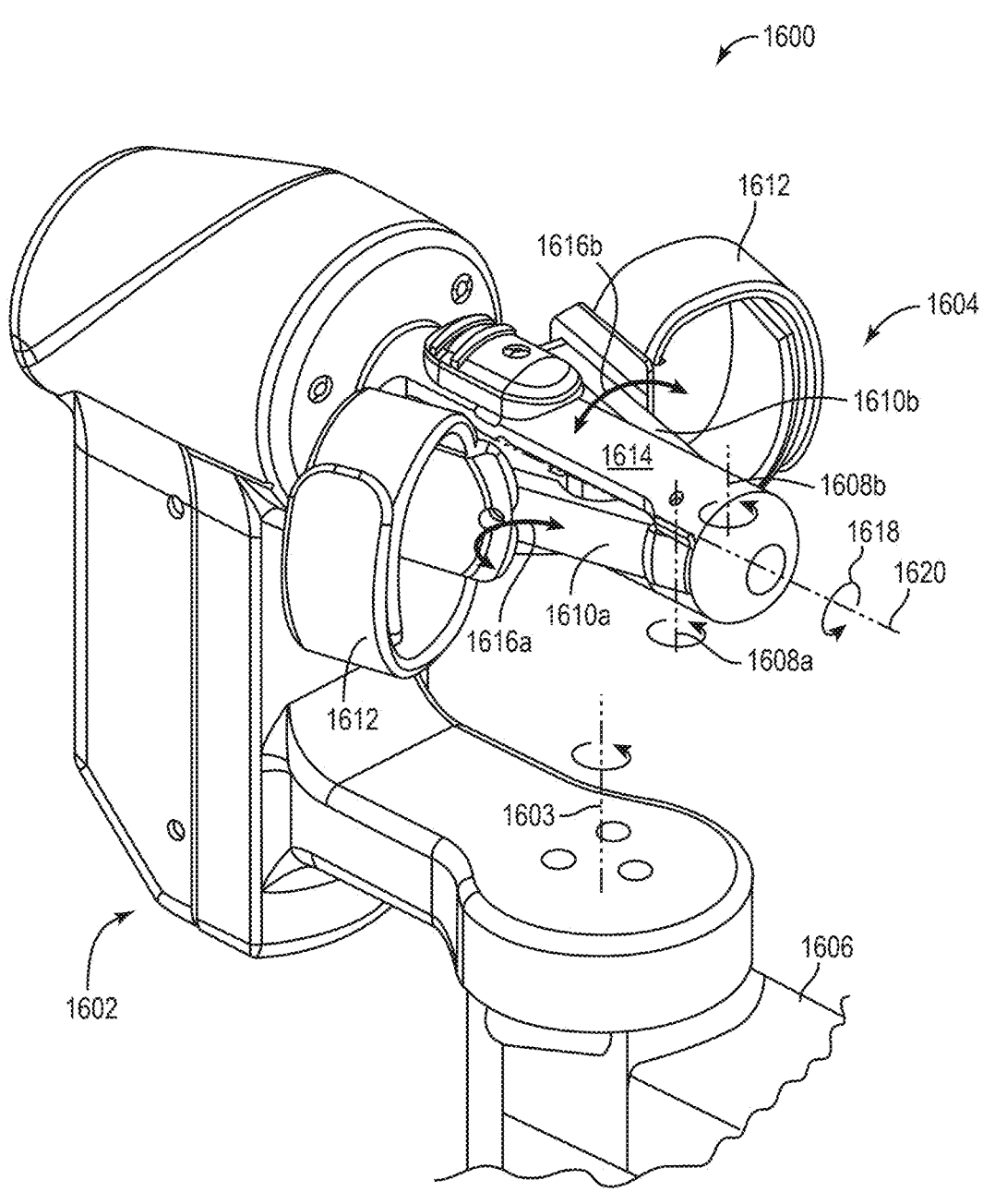
FIG. 16 is a perspective view of an example control input device that can be used in the arm assembly of FIG. 4, according to some implementations.

FIG. 16 is a perspective view of an example control input device 1600 which can be used in conjunction with one or more features described herein. In some implementations, control input device 1600 can be control input device 408 as described above with reference to FIGS. 4 and 12. For example, user input can be provided via control input device 1600 to control one or more controllable device functions. For example, in a teleoperated system, the control input device can control a manipulator device as described above, or can be included in a different control system.

Control input device 1600 can include support member 1602 (e.g., similar to support member 424 of FIG. 4) and grip portion 1604 (e.g., similar to grip portion 426 of FIG. 4). Support member 1602 extends horizontally and vertically in an approximate "L" shape, and grip portion 1604 is rotatably coupled to member 1602. In the described implementation, support member 1602 rotates about an axis 1603 with respect to a link 1606, which can be similar to second link 414 of FIG. 4 in some implementations. Axis 1603 can be similar to axis 428 shown in FIG. 4.

Grip portion 1604 is contacted by a user to manipulate the control input device. Grip portion 1604 includes two grip members 1610 (grip members 1610a and 1610b) that each include a finger loop 1612. The two grip members 1610 are positioned on opposite sides of a central portion 1614 of the grip portion 1604, and the grip members 1610 can be grasped, held, or otherwise contacted by a user's fingers. Each finger loop 1612 can secure a user's fingers to the associated grip member 1610. Each grip member 1610 is rotatably coupled to central portion 1614 and pivoted in a respective rotational degree of freedom 1616a and 1616b. For example, the grip members 1610 can be pivoted simultaneously in a pincher-type of movement. In some examples, the orientations of grip members 1610 in their degrees of freedom can control corresponding rotational positions of an end effector or component thereof of a manipulator system 204. Grip portion 1604 can be provided with a rotational degree of freedom 1618 about a longitudinal roll axis 1620 that extends approximately along the center of the central portion 1614 of grip portion 1604.

In some implementations, one or more grip sensors can be coupled to the grip portion 1604 and/or other components of device 1600 and can detect orientations of the grip members 1610a and 1610b in their degrees of freedom 1616. The grip sensors can send signals describing sensed orientations and/or motions to one or more control circuits of the teleoperated system 200. In some implementations, the control circuits can provide control signals to a manipulator device, e.g., manipulator system 204. Various implementations of the control input device 1600 can provide one or more active actuators (e.g., motors, voice coils, etc.) to output active forces on the grip members 1610 in the degrees of freedom 1616. For example, a sensor and/or actuator can be housed in central portion 1614 or in a housing of support member 1602 and can be coupled to the grip members 1610 by a transmission. Some implementations can provide one or more passive actuators (e.g., brakes) or springs to provide resistance in particular directions of the grip members 1610. Similarly, one or more sensors can be coupled to the grip portion 1604 to detect the orientation of the grip portion in the rotational degree of freedom 1618. Some implementations of the control input device 1600 can provide one or more actuators to output forces on the grip portion 1604 (including grip members 1610) in the rotational degree of freedom 1618.

Figure 17:
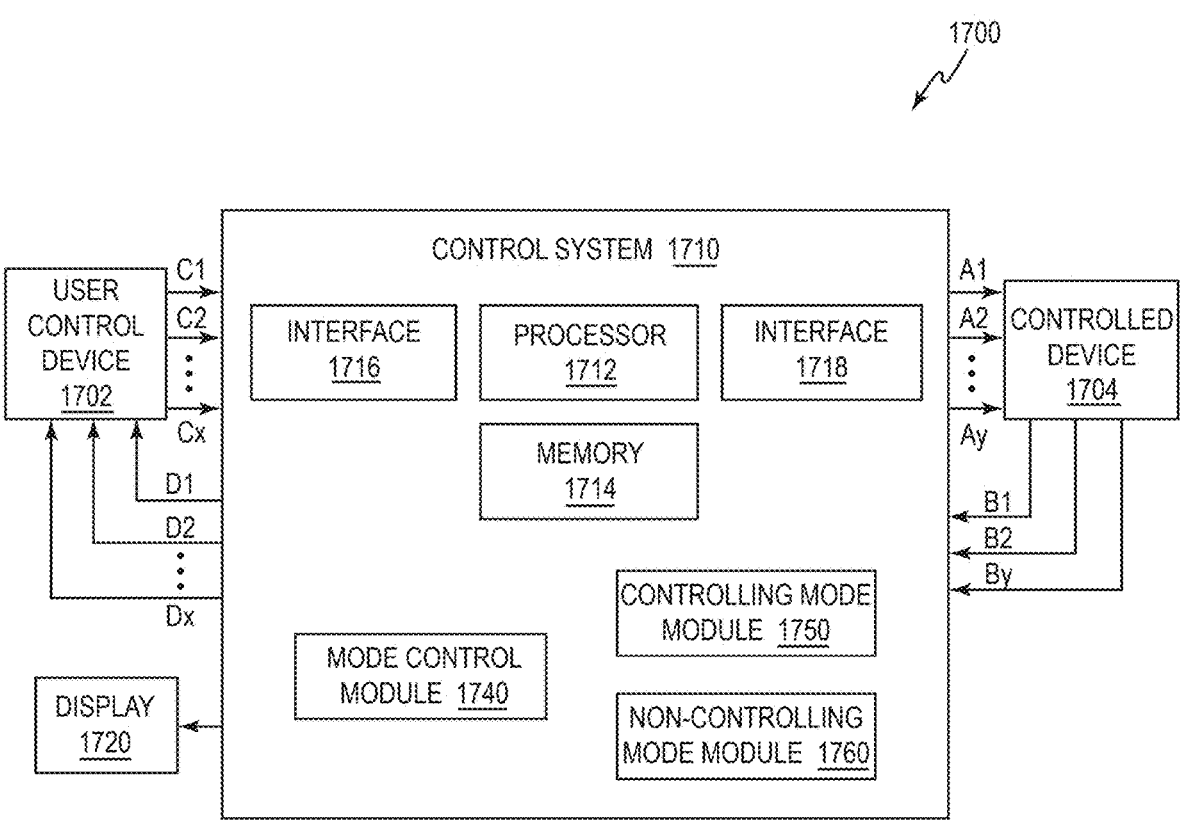
FIG. 17 is a block diagram of an example control system which can be used in one or more implementations described herein.

FIG. 17 is a block diagram of an example control system 1700 which can be used with one or more features described herein. System 1700 includes a user control device 1702 that a user may manipulate in order to control a controlled device 1704 in communication with the user control device 1702. In some implementations, user control device 1702 can be, or can be included in, user control system 202 of FIG. 2. In some implementations, controlled device 1704 can be, or can be included in, manipulator system 204 of FIG. 2. More generally, user control device 1702 can include, or be a portion of, any type of control input device that can be physically manipulated by a user (e.g., control input device 408). User control device 1702 generates control signals C1 to Cx indicating positions, states, and/or changes of one or more control input devices in their degrees of freedom. The user control device 1702 can also generate control signals (not shown) indicating selection of physical buttons and other manipulations by the user.

A control block 1710 can be included in the user control device 1702, in the controlled device 1704, or in a separate device, e.g., an intermediary device between user control device 1702 and controlled device 1704. In some implementations, the control block 1710 can be distributed among multiple of these devices. Control block 1710 receives control signals C1 to Cx and generates actuation signals A1 to Ay, which are sent to controlled device 1704. Control block 1710 can also receive sensor signals B1 to By from the controlled device 1704 that indicate positions, states, and/or changes of various components of the controlled device (e.g., manipulator arm members, instruments, or other elements). Control block 1710 can include general components such as a processor 1712, memory 1714, and interface hardware 1716 and 1718 for communication with user control device 1702 and controlled device 1704, respectively. Processor 1712 can execute program code and control basic operations of the system 1700, including functions related to sensing orientations of arm members and sending signals to control motors as described herein, and can include one or more processors of various types, including microprocessors, application specific integrated circuits (ASICs), and other electronic circuits. Memory 1714 can store instructions for execution by the processor and can include any suitable processor-readable storage medium, e.g., random access memory (RAM), read-only memory (ROM), Electrical Erasable Read-only Memory (EE-PROM), Flash memory, etc. Various other input and output devices can also be coupled to the control block 1710, e.g., display(s) 1720 such as the viewer 1713 of the user control system 202 and/or display 224 of FIGS. 2 and 3.

In this example, control block 1710 includes a mode control module 1740, a controlling mode module 1750, and a non-controlling mode module 1760. Other implementations can use other modules, e.g., a force output control module, sensor input signal module, etc. In some implementations, the modules 1740, 1750, and 1760 can be implemented using the processor 1712 and memory 1714, e.g., program instructions stored in memory 1714 and/or other memory or storage devices connected to control block 1710.

Mode control module 1740 can detect when a user initiates a controlling mode and a non-controlling mode of the system, e.g., by user selection of controls, sensing a presence of a user at a user control system or control input device, sensing required manipulation of a control input device, etc. The mode control module can set the controlling mode or a non-controlling mode of the control system 1710 based on one or more control signals C1 to Cx.

In some implementations, controlling mode module 1750 may be used to control a controlling mode of control block 1710. Controlling mode module 1750 can receive control signals C1 to Cx and can generate actuation signals A1 to Ay that control actuators of the controlled device 1704 and cause it to follow the movement of user control device 1702, e.g., so that the movements of controlled device 1704 correspond to a mapping of the movements of user control device 1702. Controlling mode module 1750 can also be used to control forces on the user control device 1702, e.g., forces output on one or more components of the arm assembly of the user control device, e.g., base element, arm members, grip members, etc., using one or more control signals D1 to Dx output to actuator(s) used to apply forces to the components, e.g., on arm links of the arm 302, to link members and/or grip members of the control input device 304, etc. In some examples, control signals D1 to Dx can be used to provide force feedback, gravity compensation, etc.

In some implementations, a non-controlling mode module 1760 may be used to control a non-controlling mode of system 1700. In the non-controlling mode, movement in one or more degrees of freedom of user control device 1702, or other manipulations of user control device 1702, has no effect on the movement of one or more components of controlled device 1704. In some implementations, non-controlling mode can include one or more other operating modes of the control block 1710, e.g., a selection mode in which movement of a control input device of user control device 1702 in one or more of its degrees of freedom and/or selection of the control switches of the control input device can control selection of displayed options, e.g., in a graphical user interface displayed by display device 1720 and/or other device. A viewing mode can allow movement of the control input device to control a display provided from cameras, or movement of cameras, that may not be included in the controlled device 1704. Control signals C1 to Cx can be used by the non-controlling mode module 1760 to control such elements (e.g., cursor, views, etc.) and control signals D1 to Dx can be determined by the non-controlling mode module to cause output of forces on the control input device during such non-controlling modes, e.g., to indicate to the user interactions or events occurring during such modes.

Some implementations described herein can be implemented or assisted, at least in part, by computer program instructions or code which can be executed on a computer. For example, the code can be implemented by one or more digital processors (e.g., microprocessors or other processing circuitry). Instructions can be stored on a computer program product including a non-transitory computer readable medium (e.g., storage medium), where the computer readable medium can include a magnetic, optical, electromagnetic, or semiconductor storage medium including semiconductor or solid state memory, magnetic tape, a removable computer diskette, a random access memory (RAM), a read-only memory (ROM), flash memory, a rigid magnetic disk, an optical disk, a memory card, a solid-state memory drive, etc. The media may be or be included in a server or other device connected to a network such as the Internet that provides for the downloading of data and executable instructions. Alternatively, implementations can be in hardware (logic gates, etc.), or in a combination of hardware and software. Example hardware can be programmable processors (e.g. Field-Programmable Gate Array (FPGA), Complex Programmable Logic Device), general purpose processors, graphics processors, Application Specific Integrated Circuits (ASICs), and the like.

The functional blocks, operations, features, methods, devices, and systems described in the present disclosure may be integrated or divided into different combinations of systems, devices, and functional blocks.

Although the present implementations have been described in accordance with the examples shown, there can be variations to the implementations and those variations are within the spirit and scope of the present disclosure. Accordingly, many modifications may be made without departing from the spirit and scope of the appended claims.

What is claimed is:

1. A counterbalance apparatus comprising:
a spring;
a tension element including a first end coupled to the spring and a second end coupled to a mechanical ground;
a base element rigidly coupled to a load;
a configurable arm rotatably coupled to the base element, the configurable arm being rotatable about a first axis; and
one or more pulleys rotatably coupled to the configurable arm,
wherein a particular pulley of the one or more pulleys is orbitable about the first axis;
wherein the tension element is at least partially wrapped around the one or more pulleys;
wherein the configurable arm is rotatably configurable about the first axis at a first orientation and a second orientation; and
wherein the first orientation is associated with a center of gravity of the load located on a first side of the counterbalance apparatus, and the second orientation is associated with the center of gravity of the load located on a second side of the counterbalance apparatus opposite to the first side.

2. The counterbalance apparatus of claim 1, wherein:
the particular pulley is rotatable about a second axis.

3. The counterbalance apparatus of claim 2, wherein:
the configurable arm and the particular pulley are positioned such that a third axis intersects the first axis, the second axis, and the center of gravity of the load.

4. The counterbalance apparatus of claim 2, wherein:
the configurable arm includes a length; and
the length is aligned with a third axis that intersects the first axis, the second axis, and the center of gravity of the load.

5. The counterbalance apparatus of claim 2, wherein:
the counterbalance apparatus further includes a first stop member associated with the first orientation of the configurable arm and a second stop member associated with the second orientation of the configurable arm;
the first stop member is located in a path of clockwise rotation of the configurable arm about the first axis; and
the second stop member is located in a path of counterclockwise rotation of the configurable arm about the first axis.

6. The counterbalance apparatus of claim 1, wherein:
the configurable arm is rotatably configurable to the first orientation and to the second orientation independently from an orientation of the load with respect to the counterbalance apparatus.

7. The counterbalance apparatus of claim 1, further comprising a rotatable shaft having a length and an axis of rotation about the length, wherein:

the base element is a joint gear rigidly coupled to the rotatable shaft;

the configurable arm is rotatably coupled to the rotatable shaft; and an axis of rotation of the particular pulley is offset from the axis of rotation of the rotatable shaft.

8. The counterbalance apparatus of claim 1, wherein:

the base element includes a first slot and a second slot;

the configurable arm engages with the first slot at the first orientation of the configurable arm without engaging with the second slot; and the configurable arm engages with the second slot at the second orientation of the configurable arm without engaging with the first slot.

9. The counterbalance apparatus of claim 8, wherein:

the configurable arm includes a plug portion;

the plug portion includes first tapered sides;

the first slot of the base element includes one or more second tapered sides;

the second slot of the base element includes one or more third tapered sides; and the first tapered sides of the plug portion are engageable with the one or more second tapered sides of the first slot and with the one or more third tapered sides of the second slot of the base element.

10. The counterbalance apparatus of claim 1, wherein:

the configurable arm includes a first aperture, and the first aperture includes a threaded portion and a clearance portion;

the base element includes a second aperture; and the counterbalance apparatus further includes a bolt extending through the particular pulley, through the first aperture of the configurable arm, and into the second aperture of the base element.

11. The counterbalance apparatus of claim 1, wherein:

the first orientation of the configurable arm counterbalances the center of gravity of the load located on the first side of the counterbalance apparatus; and the second orientation of the configurable arm counterbalances the center of gravity of the load located on the second side of the counterbalance apparatus.

12. The counterbalance apparatus of claim 1, wherein:

the tension element is a cable.

13. The counterbalance apparatus of claim 1, wherein:

the particular pulley is a first pulley;

the one or more pulleys further include a second pulley rotatably coupled to the configurable arm and rotatable about the first axis, and a third pulley rotatably coupled to the mechanical ground;

the tension element is wrapped at least partially around the third pulley prior to being wrapped around the first pulley in a path from the first end to the second end of the tension element; and the third pulley has an axis of rotation that is fixed in a same position relative to the second pulley at both the first orientation and the second orientation of the configurable arm.

14. The counterbalance apparatus of claim 1, wherein the configurable arm is:

fixed in rotation with reference to the base element when at the first orientation and when at the second orientation, and rotatable between the first orientation and the second orientation with respect to the base element when at an orientation of the configurable arm other than the first orientation and the second orientation.

15. The counterbalance apparatus of claim 2, wherein:

the particular pulley is a first pulley;

the counterbalance apparatus further includes a curved element that includes a curved surface, the curved element coupled to the mechanical ground;

the one or more pulleys further include a second pulley and a third pulley;

the second pulley is rotatable about the first axis;

the third pulley is rotatably coupled to the curved element and is rotatable about a third axis of rotation that is nonparallel to the first axis and the second axis;

in a path from the first end to the second end of the tension element, the tension element is wrapped at least partially around the third pulley prior to being wrapped around the first pulley, and the tension element is at least partially wrapped around the curved element prior to being coupled to the mechanical ground at the second end of the tension element; and along the path from the first end to the second end of the tension element, the tension element exits contact with the third pulley and enters contact with the curved surface of the curved element at points located within a plane that intersects the second pulley and the first pulley.

16. The counterbalance apparatus of claim 15, wherein:

the plane is orthogonal to the first axis and the second axis; and the third axis of rotation is at a non-orthogonal angle with reference to the plane.

17. The counterbalance apparatus of claim 15, wherein:

the curved element is rigidly coupled to the mechanical ground, is centered on the third axis, and is located between the third pulley and the mechanical ground; and the curved surface of the curved element has a radius equal to a radius of the third pulley.

18. The counterbalance apparatus of claim 15, further comprising a fourth pulley rotatably coupled to the mechanical ground and rotatable about a fourth axis, wherein:

the tension element is wrapped at least partially around the fourth pulley prior to being wrapped around the third pulley in the path from the first end to the second end of the tension element; and the fourth axis is nonparallel to the first axis, the second axis, and the third axis.

19. The counterbalance apparatus of claim 1, wherein:

the configurable arm includes an edge and a slot in the edge; and the slot is configured to receive a separation tool to slide or pry the configurable arm away from the base element.

20. The counterbalance apparatus of claim 1, wherein:

the counterbalance apparatus is included in a component of a teleoperated surgical system.

* * * * *